US012071637B2

(12) United States Patent
Yang et al.

(10) Patent No.: US 12,071,637 B2
(45) Date of Patent: Aug. 27, 2024

(54) **METHOD OF PRODUCING VALUE-ADDED CHEMICALS BY USING *CLOSTRIDIUM* AND *BACILLUS* CO-CULTURES**

(71) Applicant: National University of Singapore, Singapore (SG)

(72) Inventors: Kun-Lin Yang, Singapore (SG); Kang Zhou, Singapore (SG); Yonghao Cui, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 17/740,550

(22) Filed: May 10, 2022

(65) Prior Publication Data

US 2022/0372449 A1 Nov. 24, 2022

(30) Foreign Application Priority Data

May 10, 2021 (SG) ........................... 10202104851Y

(51) Int. Cl.

| | |
|---|---|
| ***C12N 9/04*** | (2006.01) |
| ***C12N 1/21*** | (2006.01) |
| ***C12N 9/20*** | (2006.01) |
| ***C12P 7/04*** | (2006.01) |
| ***C12P 7/16*** | (2006.01) |

(52) U.S. Cl.

CPC ............. *C12N 9/0006* (2013.01); *C12N 9/20* (2013.01); *C12P 7/04* (2013.01); *C12P 7/16* (2013.01)

(58) Field of Classification Search

None

See application file for complete search history.

(56) References Cited

U.S. PATENT DOCUMENTS

2019/0218505 A1* 7/2019 Papoutsakis .............. C12P 7/16

OTHER PUBLICATIONS

Cui et al., Aerobic acetone-butanol-isopropanol (ABI) fermentation through a co-culture of Clostridium beijerinckii G117 and recombinant Bacillus subtilis 1A1, Metabolic Eng. Comm. 11, 2020, e00137. (Year: 2020).*

Brault G, Shareck F, Hurtubise Y, et al (2014) Short-chain flavor ester synthesis in organic media by an *E. coli* whole- cell biocatalyst expressing a newly characterized heterologous lipase. PLoS One 9. <doi.org/10.1371/journal.pone.0091872>.

Chua TK, Liang DW, Qi C, Yang KL, He J (2013) Characterization of a butanol-acetone-producing Clostridium strain and identification of its solventogenic genes. Bioresour Technol 135:372-378. <doi.org/10.1016/j.biortech.2012.08.085>.

Detman A, Mielecki D, Chojnacka A, Salamon A, Blaszczyk MK, Sikora A (2019) Cell factories converting lactate and acetate to butyrate: Clostridium butyricum and microbial communities from dark fermentation bioreactors. Microb Cell Fact 18:1-12. <doi.org/10.1186/s12934-019-1085-1>.

Devi NA, Radhika GB, Bhargavi RJ (2017) Lipase catalyzed transesterification of ethyl butyrate synthesis in n-hexane—a kinetic study. J Food Sci Technol 54:2871-2877. https://doi.org/10.1007/s13197-017-2725-2.

Dusséaux S, Croux C, Soucaille P, Meynial-Salles I (2013) Metabolic engineering of Clostridium acetobutylicum ATCC 824 for the high-yield production of a biofuel composed of an isopropanol/butanol/ethanol mixture. Metab Eng 18:1-8. <doi.org/10.1016/j.ymben.2013.03.003>.

Dwidar M, Kim S, Jeon BS, Um Y, Mitchell RJ, Sang BI (2013) Co-culturing a novel Bacillus strain with Clostridium tyrobutyricum ATCC 25755 to produce butyric acid from sucrose. Biotechnol Biofuels 6:1. <doi.org/10.1186/1754-6834-6-35>.

Hou X, From N, Angelidaki I, Huijgen WJJ, Bjerre AB (2017) Butanol fermentation of the brown seaweed Laminaria digitata by Clostridium beijerinckii DSM-6422. Bioresour Technol 238:16-21. <doi.org/10.1016/j.biortech.2017.04.035>.

Jiang Y, Xu C, Dong F, Yang Y, Jiang W, Yang S (2009) Disruption of the acetoacetate decarboxylase gene in solvent-producing Clostridium acetobutylicum increases the butanol ratio. Metab Eng 11:284-291. <doi.org/10.1016/j.ymben.2009.06.002>.

Joseph RC, Kim NM, Sandoval NR (2018) Recent developments of the synthetic biology toolkit for Clostridium. Front Microbiol 9:1-13. <doi.org/10.3389/fmicb.2018.00154>.

Kirk O, Christensen MW (2002) Lipases from Candida antarctica: Unique biocatalysts from a unique origin. Org Process Res Dev 6:446-451. <doi.org/10.1021/op0200165>.

Kiyoshi, K., Furukawa, M., Seyama, T., Kadokura, T., Nakazato, A., Nakayama, S., 2015. Butanol production from alkali-pretreated rice straw by co-culture of Clostridium thermocellum and Clostridium saccharoperbutylacetonicum. Bioresour. Technol. 186, 325-328. <doi.org/10.1016/j.biortech.2015.03.061>.

Lee J, Jang YS, Choi SJ, Im JA, Song H, Cho JH, Seung DY, Terry Papoutsakis E, Bennett GN, Lee SY (2012) Metabolic engineering of clostridium acetobutylicum ATCC 824 for isopropanol-butanol-ethanol fermentation. Appl Environ Microbiol 78:1416-1423. <doi.org/10.1128/AEM.06382-11>.

(Continued)

*Primary Examiner* — Todd M Epstein

(74) *Attorney, Agent, or Firm* — Patterson + Sheridan, LLP

(57) ABSTRACT

The present invention relates to a composition or combination for the production of butanol and isopropanol, comprising an acetone-butanol-ethanol (ABE)-producing *Clostridium* strain and a genetically engineered *B. subtilis* strain, wherein said genetically engineered *B. subtilis* strain has been transformed by at least one polynucleotide molecule; the at least one polynucleotide molecule comprising a secondary alcohol dehydrogenase gene operably linked to at least one promoter. The invention also relates to methods of producing butanol and isopropanol in a co-culture, methods of producing butyrate, isopropanol and butanol in a co-culture and methods of producing esters.

13 Claims, 14 Drawing Sheets

Specification includes a Sequence Listing.

(56) References Cited

OTHER PUBLICATIONS

Lee SY, Park JH, Jang SH, Nielsen LK, Kim J, Jung KS (2008) Fermentative butanol production by clostridia. Biotechnol Bioeng 101:209-228. <doi.org/10.1002/bit.22003>.
Lehmann D, Honicke D, Ehrenreich A, Schmidt M, Weuster-Botz D, Bahl H, Lütke-Eversloh T (2012) Modifying the product pattern of Clostridium acetobutylicum: Physiological effects of disrupting the acetate and acetone formation pathways. Appl Microbiol Biotechnol 94:743-754. <doi.org/10.1007/s00253-011-3852-8>.
Li L,, Ai H, Zhang S, Li S, Liang Z, Wu ZQ, Yang ST, Wang JF (2013) Enhanced butanol production by coculture of Clostridium beijerinckii and Clostridium tyrobutyricum. Bioresour Technol 143:397-404. <doi.org/10.1016/j.biortech.2013.06.023>.
Liu J, Li Z (2019) Enhancing cofactor recycling in the bioconversion of racemic alcohols to chiral amines with alcohol dehydrogenase and amine dehydrogenase by coupling cells and cell-free system. Biotechnol Bioeng 116:536-542. <doi.org/10.1002/bit.26896>.
Li, Q., Guo, C., Liu, C.Z., 2014. Dynamic microwave-assisted alkali pretreatment of cornstalk to enhance hydrogen production via co-culture fermentation of Clostridium thermocellum and Clostridium thermosaccharolyticum. Biomass and Bioenergy 64, 220-229. <doi.org/10.1016/j.biombioe.2014.03.053>.
Liu X, Zhu Y, Yang ST (2006) Butyric acid and hydrogen production by Clostridium tyrobutyricum ATCC 25755 and mutants. Enzyme Microb Technol 38:521-528. <doi.org/10.1016/j.enzmictec.2005.07.008>.
Ma X, Liang H, Cui X, Liu Y, Lu H, Ning W, Poon NY, Ho B, Zhou K (2019) A standard for near-scarless plasmid construction using reusable DNA parts. Nat Commun 10:1-12. <doi.org/10.1038/s41467-019-11263-0>.
Mi S, Gu C, Wu P, Liu H, Yan X, Li D, Tang X, Duan X, Wang G, Zhang J (2018) Improvement of butanol production by the development and co-culture of C. acetobutylicum TSH1 and B. cereus TSH2. Appl Microbiol Biotechnol 102:6753-6763. <doi.org/10.1007/s00253-018-9151-x>.
Mühlmann M, Forsten E, Noack S, Büchs J (2017) Optimizing recombinant protein expression via automated induction profiling in microtiter plates at different temperatures. Microb Cell Fact 16:1-12. <doi.org/10.1186/s12934-017-0832-4>.
Ng CH, Yang KL (2016) Lipase in biphasic alginate beads as a biocatalyst for esterification of butyric acid and butanol in aqueous media. Enzyme Microb Technol 82:173-179. <doi.org/10.1016/j.enzmictec.2015.10.005>.
Noh HJ, Woo JE, Lee SY, Jang YS (2018) Metabolic engineering of Clostridium acetobutylicum for the production of butyl butyrate. Appl Microbiol Biotechnol 102:8319-8327. <doi.org/10.1007/s00253-018-9267-z>.
Oliva-Rodríguez AG, Quintero J, Medina-Morales MA, Morales-Martinez TK, Rodríguez-De la Garza JA, Moreno-Dávila M, Aroca G, Rios González LJ (2019) Clostridium strain selection for co-culture with Bacillus subtilis for butanol production from agave hydrolysates. Bioresour Technol 275:410-415. <doi.org/10.1016/j.biortech.2018.12.085>.
Rassadin VG, Likhterova NM, Slavin VN, Zharov A V (2006) Problems in production of high-octane, unleaded automotive gasolines. Chem Technol fuels oils 42:235-242.
Rodriguez GM, Tashiro Y, Atsumi S (2014) Expanding ester biosynthesis in *Escherichia coli*. Nat Chem Biol 10:259-265. <doi.org/10.1038/nchembio.1476>.
Romero S, Merino E, Bolívar F, Gosset G, Martinez A (2007) Metabolic engineering of Bacillus subtilis for ethanol production: Lactate dehydrogenase plays a key role in fermentative metabolism. Appl Environ Microbiol 73:5190-5198. <doi.org/10.1128/AEM.00625-07>.
Rude MA, Schirmer A (2009) New microbial fuels: a biotech perspective. Curr Opin Microbiol 12:274-281. <doi.org/10.1016/j.mib.2009.04.004>.
Sillers R, Al-Hinai MA, Papoutsakis ET (2009) Aldehyde-alcohol dehydrogenase and/or thiolase overexpression coupled with CoA transferase downregulation lead to higher alcohol titers and selectivity in clostridium acetobutylicum fermentations. Biotechnol Bioeng 102:38-49. <doi.org/10.1002/bit.22058>.
Stergiou PY, Foukis A, Filippou M, et al (2013) Advances in lipase-catalyzed esterification reactions. Biotechnol Adv 31:1846-1859. <doi.org/10.1016/j.biotechadv.2013.08.006>.
Survase SA, Jurgens G, Van Heiningen A, Granstrom T (2011) Continuous production of isopropanol and butanol using Clostridium beijerinckii DSM 6423. Appl Microbiol Biotechnol 91:1305-1313. <doi.org/10.1007/s00253-011-3322-3>.
Tran HTM, Cheirsilp B, Hodgson B, Umsakul K (2010) Potential use of Bacillus subtilis in a co-culture with Clostridium butylicum for acetone-butanol-ethanol production from cassava starch. Biochem Eng J 48:260-267. <doi.org/10.1016/i.bej.2009.11.001>.
Van den Berg C, Heeres AS, van der Wielen LAM, Straathof AJJ (2013) Simultaneous clostridial fermentation, lipase-catalyzed esterification, and ester extraction to enrich diesel with butyl butyrate. Biotechnol Bioeng 110:137-142. <doi.org/10.1002/bit.24618>.
Wang Y, Wang Z, Xu Q, Du G, Hua Z, Liu L, Li J, Chen J (2009) Lowering induction temperature for enhanced production of polygalacturonate lyase in recombinant Pichia pastoris. Process Biochem 44:949-954. <doi.org/10.1016/i.procbio.2009.04.019>.
Wu P, Wang G, Wang G, Børresen BT, Liu H, Zhang J (2016) Butanol production under microaerobic conditions with a symbiotic system of Clostridium acetobutylicum and Bacillus cereus. Microb Cell Fact 15:1-11. <doi.org/10.1186/s12934-016-0412-z>.
Xin F, Basu A, Yang KL, He J (2016) Strategies for production of butanol and butyl-butyrate through lipase-catalyzed esterification. Bioresour Technol 202:214-219. <doi.org/10.1016/j.biortech.2015.11.068>.
Xin F, Chen T, Jiang Y, Dong W, Zhang W, Zhang M, Wu H, Ma J, Jiang M (2017) Strategies for improved isopropanol-butanol production by a Clostridium strain from glucose and hemicellulose through consolidated bioprocessing. Biotechnol Biofuels 10:1-13. <doi.org/10.1186/s13068-017-0805-1>.
Xin F, Dong W, Jiang Y, et al (2018) Recent advances on conversion and co-production of acetone-butanol-ethanol into high value-added bioproducts. Crit Rev Biotechnol 38:529-540. <doi.org/10.1080/07388551.2017.1376309>.
Xin F, He J (2013) Characterization of a thermostable xylanase from a newly isolated Kluyvera species and its application for biobutanol production. Bioresour Technol 135:309-315. <doi.org/10.1016/j.biortech.2012.10.002>.
Youn SH, Lee KM, Kim KY, Lee SM, Woo HM, Um Y (2016) Effective isopropanol-butanol (IB) fermentation with high butanol content using a newly isolated *Clostridium* sp. A1424. Biotechnol Biofuels 9:1-16. <doi.org/10.1186/s13068-016-0650-7>.
Yu M, Zhang Y, Tang IC, Yang ST (2011) Metabolic engineering of Clostridium tyrobutyricum for n-butanol production. Metab Eng 13:373-382. <doi.org/10.1016/j.ymben.2011.04.002>.
Zhang C, Li T, He J (2018) Characterization and genome analysis of a butanol-isopropanol-producing Clostridium beijerinckii strain BGS1 06 Biological Sciences 0605 Microbiology 06 Biological Sciences 0604 Genetics. Biotechnol Biofuels 11:1-11. <doi.org/10.1186/s13068-018-1274-x>.
Zhang ZT, Taylor S, Wang Y (2017) In situ esterification and extractive fermentation for butyl butyrate production with Clostridium tyrobutyricum. Biotechnol Bioeng 114:1428-1437. <doi.org/10.1002/bit.26289>.
Zhou K, Zou R, Stephanopoulos G, Too HP (2012) Enhancing solubility of deoxyxylulose phosphate pathway enzymes for microbial isoprenoid production. Microb Cell Fact 11:1-8. <doi.org/10.1186/1475-2859-11-148>.

* cited by examiner

A: protection; B: redox balancing; C: competition; D: feeding

A
Glucose
Titer (g/L)
Time (h)
B
Isopropanol
Titer (g/L)
Time (h)
C
Acetone
Titer (g/L)
Time (h)
D
Lactate
Titer (g/L)
Time (h)
E
OD600
Time (h)
BsADH2 mono-culture w/ acetone
Bs1A1 mono-culture w/ acetone
BsADH2 mono-culture w/o acetone

J

Yields relative to glucose consumption (mol/mol)

| | Acetate | Butyrate | Acetone | Isopropanol | Butanol | Alcohols | Acids | Total |
|---|---|---|---|---|---|---|---|---|
| BsADH2-CbG117 co-culture aerobic medium - Open | 0.074 | 0.125 | 0.063 | 0.014 | 0.269 | 0.283 | 0.199 | 0.545 |
| BsADH2-CbG117 co-culture aerobic medium - Closed | 0.123 | 0.192 | 0.127 | 0.065 | 0.281 | 0.346 | 0.315 | 0.789 |
| Bs1A1-CbG117 co-culture a-erobic medium - Closed | 0.096 | 0.19 | 0.197 | 0 | 0.303 | 0.303 | 0.285 | 0.786 |

a
Esters (g/L)
Time (h)
Isopropyl butyate
Butyl acetate
Butyl butyrate
b
Esters (g/L)
Time (h)
Isopropyl butyate
Butyl acetate
Butyl butyrate

METHOD OF PRODUCING VALUE-ADDED CHEMICALS BY USING *CLOSTRIDIUM* AND *BACILLUS* CO-CULTURES

CROSS-REFERENCES TO RELATED APPLICATIONS

This application claims priority to Singapore Patent Application No. 10202104851Y, filed on May 10, 2021, which is incorporated herein by reference in its entirety.

REFERENCE TO SEQUENCE LISTING

This application contains references to amino acid and nucleic acid sequences which have been submitted as the sequence listing text file entitled "SP103985US_ST25", file size 11 KiloBytes, created May 6, 2022, which is hereby incorporated by reference in its entirety.

FIELD OF THE INVENTION

The present invention relates to compositions comprising a first *Clostridium* bacteria strain and a second bacteria strain, selected from *B. subtilis* and *Clostridium*. More particularly, the first bacteria strain may be *C. beijerinckii* G117 and the second bacteria strain may be an engineered *B. subtilis* expressing a secondary alcohol dehydrogenase, preferably also a lipase; or the first bacteria strain may be *C. beijerinckii* BGS1 and the second bacteria strain may be *C. acetobutylicum* ATCC 824 or *C. tyrobutyricum*. The invention also relates to uses of such compositions for aerobic acetone-butanol-isopropanol (ABI) fermentation or for anaerobic isopropyl and butyl ester production.

BACKGROUND OF THE INVENTION

Some strains from the genus of *Clostridium* can produce acetone-butanol-ethanol (ABE) during anaerobic fermentation, which is known as ABE fermentation. However, because of the toxicity of solvents to the cells, the titers of solvents are relatively low. Acetone, which accounts for 30% of the total solvents, is regarded as an undesired product in the current ABE fermentation, due to its poor fuel properties and corrosiveness to rubber parts of engines. These issues undermine the competitiveness of the traditional ABE fermentation and impede the further development of the process.

A few studies have been reported to co-culture *Bacillus* with *Clostridium* to improve the production of butyrate, butanol or $H_2$ from substrates such as starch and glucose (Mi et al., 2018; Oliva-rodriguez et al., 2019; Tran et al., 2010; Wu et al., 2016). However, most of these studies only focused on using *Bacillus* as the oxygen consumer to provide respiratory protection so that *Clostridium* could grow. The *Bacillus* strains used in these studies are wild-type strains without being engineered.

Apart from the co-culture of *Bacillus* and *Clostridium*, the co-culture of two *Clostridium* strains has also been explored. These studies often focus on the expansion of the substrate spectrum by co-culturing two *Clostridium* strains. For example, Kiyoshi et al. (2015) managed to produce butanol from alkali-pre-treated rice straw by employing a co-culture system composed of *C. thermocellum* and *C. saccharoperbutylacetonicum* (Kiyoshi et al., 2015). Li et al. (2014) utilized co-culture of *C. thermocellum* and *C. thermosaccharolyticum* to produce hydrogen from alkali pre-treated cornstalk (Li et al., 2014). Some studies have tried to enhance butanol production by using the co-culture strategy. Li et al. reported that the production of butanol could be improved when an acidogenic species *C. tyrobutyricum* was co-cultured with a solventogenic species *C. beijerinckii.*

There is a need for bacteria culture strategies to improve yields of value-added chemicals for mass production.

SUMMARY OF THE INVENTION

The present invention relates to methods to produce more valuable products from ABE fermentation by introducing a second bacteria strain into a culture of *Clostridium*. By co-culturing *Clostridium* with an engineered *Bacillus* strain expressing a secondary alcohol dehydrogenase (CpSADH), the conventional anaerobic acetone-butanol (AB) fermentation could be shifted into the aerobic isopropanol-butanol (IB) fermentation with the production of 0.9 g/L of isopropanol and 4.8 g/L of butanol. In addition, the introduction of another *Clostridium* strain into the culture of an IBE-producing *Clostridium* helped to balance the acids/alcohols ratio, which resulted in the production of more esters in the subsequent lipase-mediated esterification stage.

The *Clostridium-Bacillus* co-culture strategy can be used for producing isopropanol and butanol without the need for costly and tedious anaerobic pre-treatment. The inventors aim to convert the traditional ABE fermentation products into other high value-added chemicals. Production of isopropanol and butanol under aerobic conditions: compared to conventional ABE fermentation that needs obligate anaerobic conditions, *Bacillus* and *Clostridium* can be co-cultured under aerobic conditions, by-passing the tedious anaerobic pre-treatments which include $N_2$ flushing and the addition of reducing agents. Moreover, acetone, which is considered as an undesired product due to its poor fuel properties and corrosiveness to the rubber parts of engines, can be reduced into isopropanol which can be used as a detergent and fuel additive. In addition, the reduction of acetone into isopropanol also further facilitates the production of short chain fatty acid esters because isopropanol can be converted into esters such as isopropyl butyrate.

The *Clostridium-Clostridium* co-culture strategy can be used for producing high value-added short chain fatty acid esters which can be used as flavor compounds aviation fuel constituent. The inventors aim to better balance the acids/alcohols ratio by co-culturing the two *Clostridium* strains so that more esters (isopropyl butyrate, butyl butyrate, and butyl acetate) could be produced from the IBE fermentation. Production of isopropyl butyrate from IBE fermentation without the addition of exogenous butyrate: traditionally, production of short chain fatty acid esters from the culture of *Clostridium* usually focuses on butyl butyrate, leading to the waste of acetone. In this *Clostridium-Clostridium* co-culture system, isopropanol, instead of acetone, was produced due to the existence of an IBE-producing strain. The isopropanol can be further converted into isopropyl butyrate by lipase. Besides, conventional production of short chain fatty acid esters requires the addition of butyrate so that the acids/alcohol ratio can be balanced, but that increases the cost. By having two *Clostridium* strains exhibiting different characteristics at pH 6, more butyrate could be produced. As a result, more esters can be produced without the need for adding butyrate.

As *Clostridium* is an anaerobe which requires obligate anaerobic conditions to grow, anaerobic pre-treatments including $N_2$ flushing and addition of reducing agents are necessary to perform the ABE fermentation. These anaerobic pre-treatments are costly and tedious. Besides, acetone, which accounts for 30% of the solvents produced, is regarded as an undesired product due to its poor fuel properties and corrosiveness to the rubber parts of the engines Therefore, it would be better if the acetone could be converted into other useful chemicals such as isopropanol. Compared with acetone, isopropanol can be used as fuel additive and detergent. Furthermore, isopropanol can also be converted into esters which are more valuable. For these reasons, the inventors developed a *Bacillus-Clostridium* co-culture system to switch the anaerobic acetone-butanol (AB) fermentation into aerobic isopropanol-butanol (IB) fermentation. This new process omits the tedious and costly anaerobic pre-treatment and enables the reduction of undesired acetone into isopropanol. Moreover, to further convert the butanol and isopropanol into short chain fatty acid esters, the inventors also created a *Clostridium-Clostridium* co-culture system which could enhance the production of short chain fatty acid esters with the addition of lipase.

In a first aspect, the present invention provides a composition or combination for the production of butanol and isopropanol, comprising an acetone-butanol-ethanol (ABE)-producing *Clostridium* strain and a genetically engineered *B. subtilis* strain, wherein said genetically engineered *B. subtilis* strain has been transformed by at least one polynucleotide molecule; the at least one polynucleotide molecule comprising a secondary alcohol dehydrogenase gene operably linked to at least one promoter.

In some embodiments, the *Clostridium* strain is *C. beijerinckii* G117.

In some embodiments, the secondary alcohol dehydrogenase gene is cpsadh.

In some embodiments, the secondary alcohol dehydrogenase gene comprises a polynucleotide sequence having at least 80% sequence identity, at least 85% sequence identity, at least 90% sequence identity, at least 95% sequence identity or 100% sequence identity, due to the degeneracy of the genetic code, to the polynucleotide sequence set forth in SEQ ID NO: 1.

In some embodiments, the secondary alcohol dehydrogenase comprises an amino acid sequence having at least 80% sequence identity, at least 85% sequence identity, at least 90% sequence identity, at least 95% sequence identity or 100% sequence identity, to the amino acid sequence set forth in SEQ ID NO: 10.

Products of the co-culture may be converted into short chain fatty acid esters by the addition of a lipase. In order to reduce costs of production, advantageously the lipase could be produced by an engineered co-culture strain. In some embodiments, one of the bacterial strains is engineered to express a lipase. Preferably the lipase-expressing strain is *B. subtilis*. Preferably the lipase is from *Candida* sp. Preferably, the engineered *B. subtilis* co-expresses the secondary alcohol dehydrogenase and a lipase.

In some embodiments, the lipase gene comprises a polynucleotide sequence having at least 80% sequence identity, at least 85% sequence identity, at least 90% sequence identity, at least 95% sequence identity or 100% sequence identity, due to the degeneracy of the genetic code, to the polynucleotide sequence set forth in SEQ ID NO: 9.

Said lipase may have the amino acid sequence set forth in SEQ ID NO: 8.

In a second aspect, the present invention provides a composition or combination for the production of isopropyl butyrate and/or butyl acetate and/or butyl butyrate, comprising a first isopropanol- and butanol-producing *Clostridium* strain and a second butyrate-producing *Clostridium* strain.

In some embodiments, the first *Clostridium* strain is *Clostridium beijerinckii* BGS1 and the second *Clostridium* strain is *Clostridium acetobutylicum* ATCC 824 or *Clostridium tyrobutyricum*.

In a third aspect, the present invention provides a method of producing butanol and isopropanol in a co-culture, comprising the steps:

a) co-culturing an acetone-butanol-ethanol (ABE)-producing *Clostridium* strain with a genetically engineered *B. subtilis* strain in medium under conditions for conventional ABE fermentation with exception that no anaerobic treatment is used, and b) supplementing the medium with glucose, wherein said genetically engineered *B. subtilis* strain has been transformed by at least one polynucleotide molecule;

the at least one polynucleotide molecule comprising a secondary alcohol dehydrogenase gene operably linked to at least one promoter, wherein the co-cultured *Clostridium* and *B. subtilis* are capable of increased production of butanol and/or isopropanol compared to a co-culture with a non-transformed *B. subtilis* cell.

In some embodiments, the secondary alcohol dehydrogenase gene is cpsadh.

In some embodiments, the secondary alcohol dehydrogenase gene comprises a polynucleotide sequence having at least 80% sequence identity, at least 85% sequence identity, at least 90% sequence identity, at least 95% sequence identity or 100% sequence identity, due to the degeneracy of the genetic code, to the polynucleotide sequence set forth in SEQ ID NO: 1.

In some embodiments, the *Clostridium* strain is *C. beijerinckii* G117.

In some embodiments, the medium is supplemented with glucose at a concentration of at least 6 g/L, at least 30 g/L, at least 60 g/L, at least 90 g/L or in the range from 30 g/L to 90 g/L, preferably in the range 50 g/L to 70 g/L.

In some embodiments, the genetically engineered *B. subtilis* strain is added to an anaerobic culture of *Clostridium* after a period of at least 8 hr, at least 16 hr, preferably at least 24 hr and co-cultured for a further period.

In some embodiments, the method further comprises isolating said butanol and/or isopropanol.

In some embodiments, the method further comprises esterification of co-culture products by the addition of a lipase. Preferably the lipase is from *Candida* sp.

In some embodiments, the method further comprises isolating said esters.

In a fourth aspect, the present invention provides a method of producing butyrate, isopropanol and butanol in a co-culture, comprising co-culturing a first isopropanol/butanol-producing *Clostridium* strain with a second butyrate-producing *Clostridium* strain in medium supplemented with glucose, at a pH of about 6.

In some embodiments, the first isopropanol/butanol-producing *Clostridium* strain is *Clostridium beijerinckii* BGS1 and said second butyrate-producing *Clostridium* strain is *Clostridium tyrobutyricum* ATCC 25755 or *Clostridium acetobutylicum* ATCC 824.

In some embodiments, at least one of said *Clostridium* strains has been engineered to produce lipase.

Preferably the lipase is from *Candida* sp. Preferably, the engineered *B. subtilis* co-expresses the secondary alcohol dehydrogenase and a lipase.

In some embodiments, the lipase gene comprises a polynucleotide sequence having at least 80% sequence identity, at least 85% sequence identity, at least 90% sequence identity, at least 95% sequence identity or 100% sequence identity, due to the degeneracy of the genetic code, to the polynucleotide sequence set forth in SEQ ID NO: 9.

Said lipase may have the amino acid sequence set forth in SEQ ID NO: 8.

In some embodiments, the method further comprises adding lipase to the medium to convert alcohols in the medium to esters.

In some embodiments, the esters produced include isopropyl butyrate, butyl butyrate and butyl acetate.

In some embodiments, the method further comprises isolating said esters.

Having now generally described the invention, the same will be more readily understood through reference to the following examples which are provided by way of illustration, and are not intended to be limiting of the present invention.

*tyrobutyricum* ATCC 25755. (c) Time profile of glucose and organic acids concentration in the mono-culture of *C. tyrobutyricum* ATCC 25755. (d) Time profile of organic solvents concentration in the mono-culture of *C. beijerinckii* BGS1. (e) Time profile of organic solvents concentration in the co-culture of *C. beijerinckii* BGS1 and *C. tyrobutyricum* ATCC 25755. (f) Time profile of $OD_{600}$ during the *C. beijerinckii* BGS1 mono-culture, *C. beijerinckii* BGS1-*C. tyrobutyricum* ATCC 25755 co-culture, and *C. tyrobutyricum* ATCC 25755 mono-culture Error bars, mean±s.e. in all graphs (some error bars are smaller than the plot symbols). There are three replicates for each data point.

Figure 14:
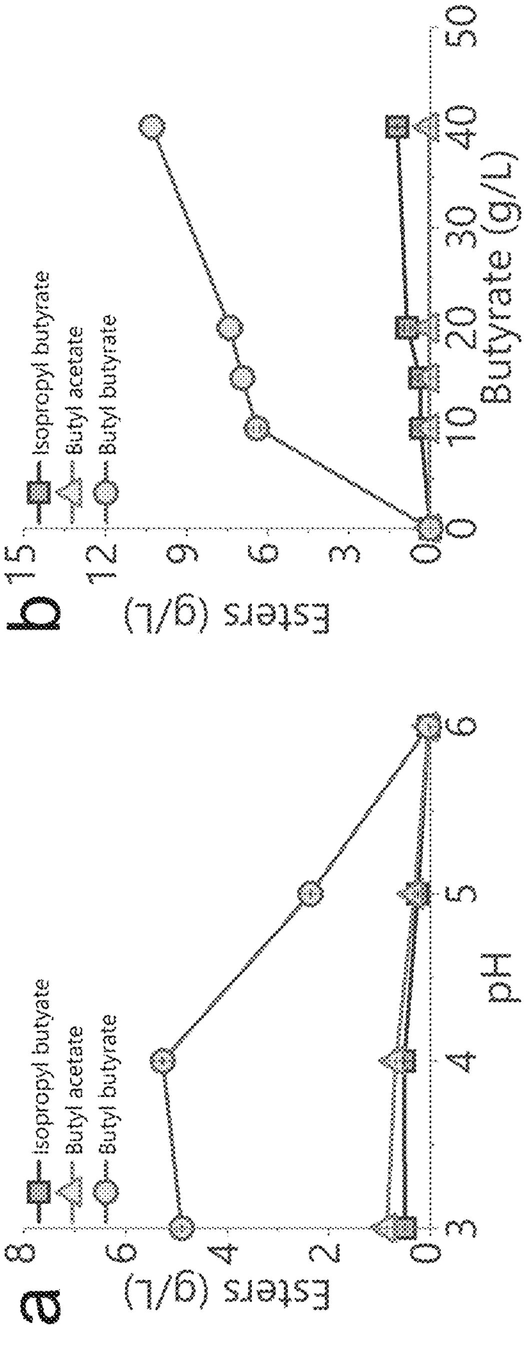

FIG. 14 shows (a) effect of pH on the production of esters. Lipase B was used. A mixture of 10 g/L butanol, 5 g/L isopropanol, 10 g/L butyric acid, and 10 g/L acetic acid was used as substrate. The reaction time was 12 hours. (b) Effect of exogenously added butyrate on the production of esters. Lipase B was used. The 120-hour cell culture of *C. beijerinckii* BGS1 was used as substrate. The reaction time was 12 hours. Error bars, mean±s.e. in all graphs (some error bars are smaller than the plot symbols). There are three replicates for each data point.

Figure 15:
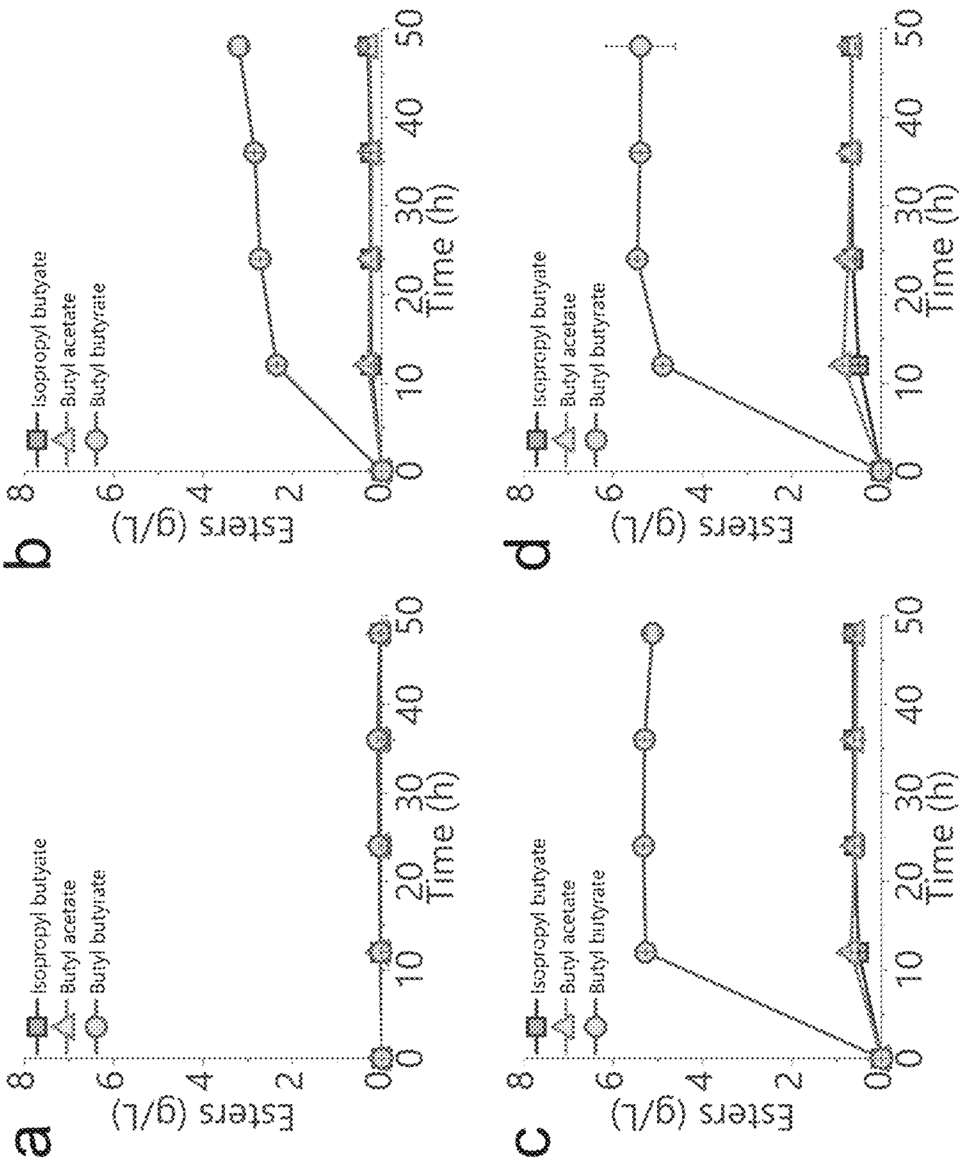

FIG. 15 shows the time profile of the esters produced at (a) pH 6. (b) pH 5. (c) pH 4. (d) pH 3. Lipase B was used. A mixture of 10 g/L butanol, 5 g/L isopropanol, 10 g/L butyric acid, and 10 g/L acetic acid was used as substrate.

Figure 16:
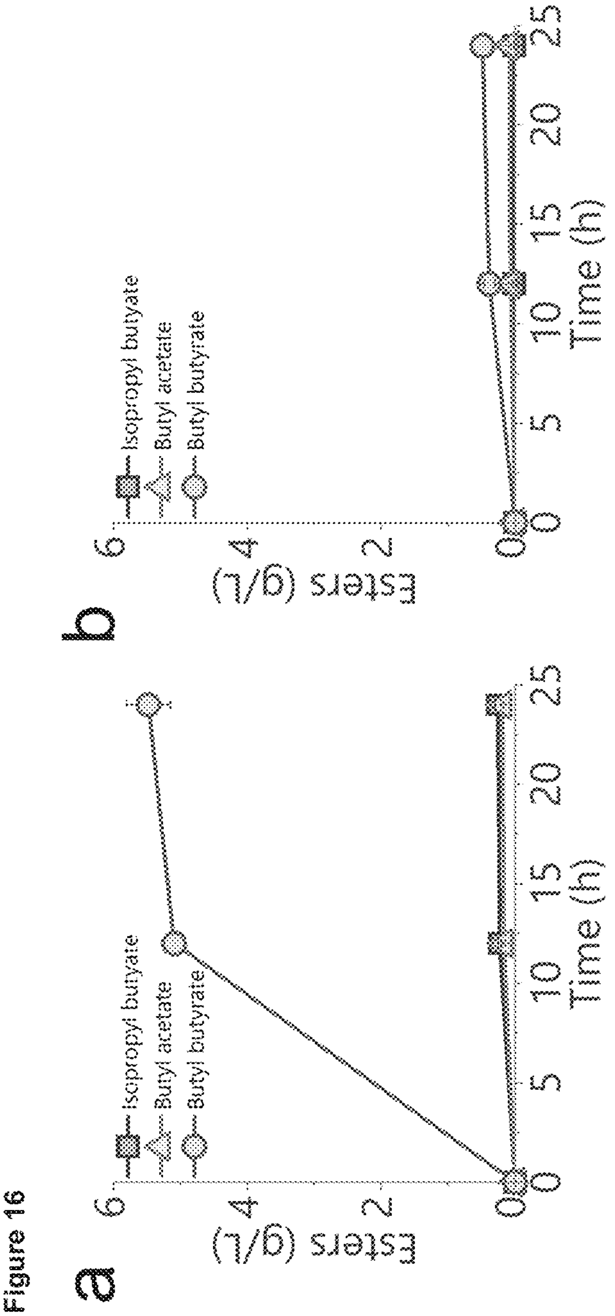

FIG. 16 shows the profile of esters from (a) co-culture of *C. beijerinckii* BGS1 and *C. tyrobutyricum* ATCC 25755 and (b) mono-culture of *C. beijerinckii* BGS1. Error bars, mean±s.e. in all graphs (some error bars are smaller than the plot symbols). There are three replicates for each data point.

Figure 17:
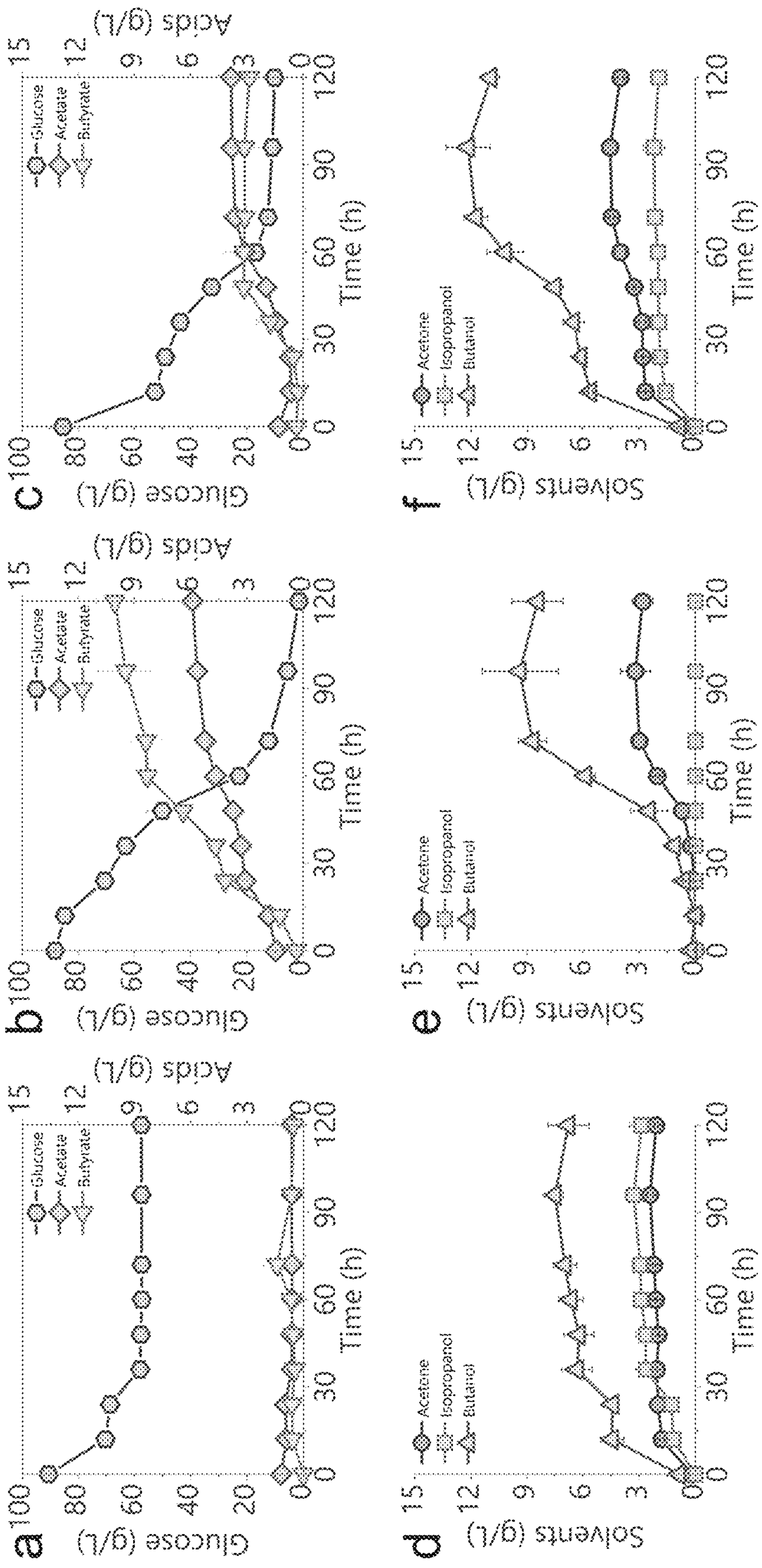

FIG. 17 shows the profile of glucose and fermentative products. (a) profile of glucose and organic acids produced in the mono-culture of *C. beijerinckii* BGS1; (b) profile of glucose and organic acids produced in the mono-culture of *C. acetobutylicum* ATCC 824; (c) profile of glucose and organic acids produced in the co-culture of *C. acetobutylicum* ATCC 824 and *C. beijerinckii* BGS1; (d) profile of organic solvents produced in the mono-culture of *C. beijerinckii* BGS1; (e) profile of organic solvents produced in the mono-culture of *C. acetobutylicum* ATCC 824; (f) profile of organic solvents produced in the co-culture of *C. acetobutylicum* ATCC 824 and *C. beijerinckii* BGS1.

Figure 18:
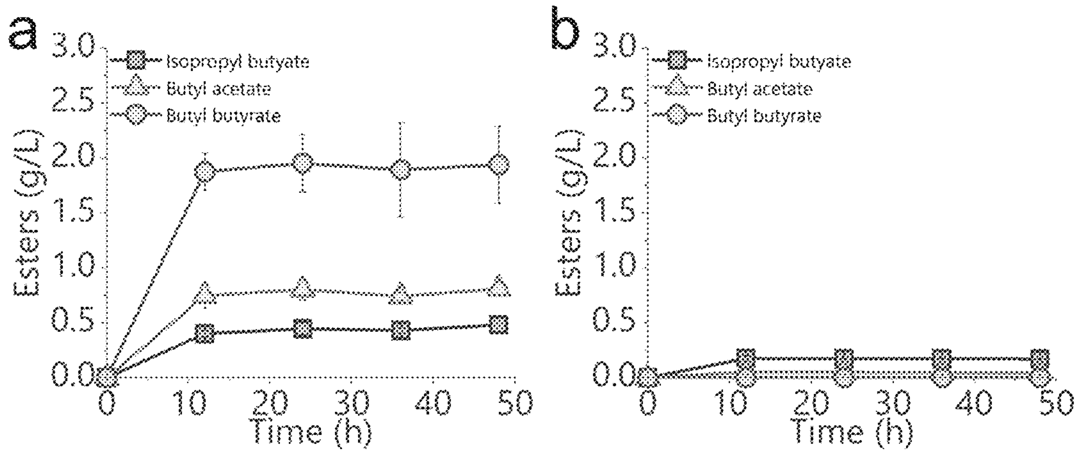

FIG. 18 shows the production of esters from (a) co-culture of *C. beijerinckii* BGS1 and *C. acetobutylicum* ATCC 824 and (b) mono-culture of *C. beijerinckii* BGS1.

DEFINITIONS

Certain terms employed in the specification, examples and appended claims are collected here for convenience.

As used in the specification and the appended claims, the singular forms "a," "an" and "the" include plural referents unless the context clearly dictates otherwise.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

The phrases "nucleic acid" or "nucleic acid sequence," as used herein, refer to an oligonucleotide, nucleotide, polynucleotide, or any fragment thereof, to DNA or RNA of genomic or synthetic origin, which may be single-stranded or double-stranded and may represent the sense or the antisense strand, to peptide nucleic acid (PNA), or to any DNA-like or RNA-like material. An example is the adh sequence set forth in SEQ ID NO: 1.

The terms "amino acid" or "amino acid sequence," as used herein, refer to an oligopeptide, peptide, polypeptide, or protein sequence, or a fragment of any of these, and to naturally occurring or synthetic molecules. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

A bacterial "strain" as used herein refers to a bacterium which remains genetically unchanged when grown or multiplied.

As used herein, the term "operably linked" means that the components to which the term is applied are in a relationship that allows them to carry out their inherent functions under suitable conditions. For example, a control sequence which is "operably linked" to a protein coding sequence is ligated thereto, so that expression of the protein coding sequence is achieved under conditions compatible with the transcriptional activity of the control sequences. By way of an example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. The Idh promoter is operably linked to the cpsadh when cpsadh is integrated into the Idh gene. Generally, operably linked DNA sequences are contiguous and, where necessary to join two protein-coding regions, in the same reading frame.

A vector can include one or more catalytic enzyme nucleic acid(s) in a form suitable for expression of the nucleic acid(s) in a host cell. Preferably the recombinant expression vector includes one or more regulatory sequences operatively linked to the nucleic acid sequence(s) to be expressed. The term "regulatory sequence" includes promoters, enhancers, ribosome binding sites and/or IRES elements, and other expression control elements (e.g., polyadenylation signals). Regulatory sequences include those which direct expression of a nucleotide sequence such as the Idh promoter driving the expression of cpsadh disclosed in the Examples herein. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., catalytic enzyme proteins such as lipase).

The recombinant expression vectors of the invention can be designed for expression of catalytic enzyme proteins in prokaryotic or eukaryotic cells, more particularly prokaryotic cells. For example, polypeptides of the invention can be expressed in bacteria (e.g., *B. subtilis* or *Clostridium* sp.). Suitable host cells are discussed further in Goeddel, (1990) Gene Expression Technology: Methods in Enzymology 185, Academic Press, San Diego, Calif.

Bibliographic references mentioned in the present specification are for convenience listed in the form of a list of references and added at the end of the examples. The whole content of such bibliographic references is herein incorporated by reference but their mention in the specification does not imply that they form part of the common general knowledge.

In some non-limiting embodiments, *C. beijerinckii* G117 refers to the isolates deposited on Sep. 9, 2014 under the Budapest Treaty with the American Type Culture Collection, 10801 University Boulevard, Manassas, Virginia 20110-2209 and assigned ATCC accession number PTA-121569. *C. beijerinckii* G117 is further described herein.

DETAILED DESCRIPTION OF THE INVENTION

Examples

Standard molecular biology techniques known in the art and not specifically described were generally followed as described in Green and Sambrook, Molecular Cloning: A Laboratory Manual, Cold Springs Harbor Laboratory, New York (2012).

Example 1

1: Aerobic Acetone-Butanol-Isopropanol (ABI) Fermentation

*Clostridium—Bacillus* Co-Culture System

Materials and Methods 1.1 Bacterial Strains

All strains and plasmids used in this study are listed in Table 1.

TABLE 1

Strains and plasmids used in this study

| Strain or plasmid | Relevant characteristics | Source or reference |
|---|---|---|
| | Strains | |
| *C. beijerinckii* G117 | Wild type strain | Chua et al. 2013 |
| Bs1A1 | Wild type *B. subtilis* 1A1 | BGSC[a] |
| *E. coli* DH5α | | NEB[b] |
| BsADH1 | *B. subtilis* 1A1 ΔIdh::operonCm | This study |
| BsADH2 | *B. subtilis* 1A1 harboring pHT01-cpsadh | This study |
| | Plasmids | |
| pHT01 | Shuttle vector; $Ap^R$, $Cm^R$ | MoBiTec |
| pHT01-cpsadh | pHT01 carrying cpadh, $Ap^R$ and $Cm^R$ | This study |
| pMB1-Idh::operonCm | pMB1 ori $Ap^R$ carrying Idh::(cpsadh $Cm^R$) | This study |

[a]*Bacillus* Genetic Stock Center;

[b]New England Biolabs;

[c] $Ap^R$, $Cm^R$ indicate resistance to ampicillin and chloramphenicol

All primers and barcodes used in constructing the pHT01-cpsadh plasmid are listed in Table 2.

TABLE 2

Primers and barcodes used in constructing the pHT01-cpsadh plasmid

| Primer or barcode | Sequence | Source or reference | SEQ ID NO: |
|---|---|---|---|
| Primer | | | |
| P01 | 5'-G*TCAATCCCGTC GTCCCAATA-3' | This study | 2 |
| P02 | 5'-A*CGGGTTAAAGA CGACGCGAC-3' | This study | 3 |
| P03 | 5'-TCCCAATTAAAGG AGGAAGGA-3' | This study | 4 |
| P04 | 5'-CTGCCCCGGGGAC GTC-3' | This study | 5 |
| Barcode | | | |
| REC3-F | 5'-TCCCAATTAAAGGA GGAAGGATCCAT*G-3' | Ma et al., 2019 | 6 |
| REC4-R | 5'-T*GATCTAGAGTCG ACGTCCCCGGGGCAG-3' | Ma et al., 2019 | 7 |

The pHT01-cpsadh plasmid was constructed by using the GT standard method (Ma et al. 2019). The cpsadh gene was amplified using P01 and P02 from a plasmid received as a gift. The sequence of cpsadh is included in the sequence listing as SEQ ID NO: 1. Then the gene was barcoded with REC3-F and REC4-R. After another round of PCR by using P03 and P04, the fragment was digested by BamHI and XbaI. Then the double-digested fragment was ligated with the pHT01 plasmid which was also digested by BamHI and XbaI.

Figure 3:
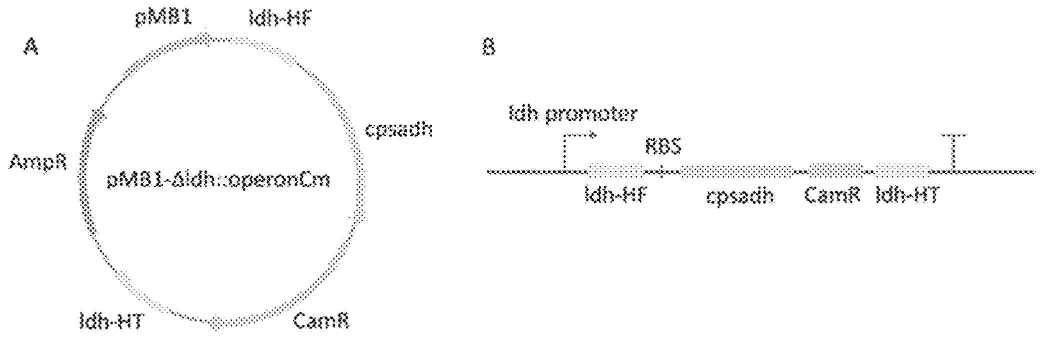
FIG. 3 shows (A) plasmid construction of pMB1-ΔIdh::operonCm and (B) illustration of the integration process.

The plasmid pMB1-Idh::operonCm was also constructed following the GT standard method below and as shown in FIG. 3.

1.2 Construction of Integrative Vector pMB1-/Dh::operonCm

In order to construct the integrative vector, a GT standard plasmid construction method was adopted (Ma et al., 2019). The chloramphenicol resistance encoding gene was amplified from pHT01 plasmid by using primers PS01 and PS02. The homologous arms Idh-HF and Idh-HT was amplified from *B. subtilis* genome by using primers PS03 and PS04, PS05 and PSO6 respectively. Notably, an RBS barcode was used between Idh-HF and cpsadh. An I-CeuI barcode was used between Idh-HT and AmpR gene so that the plasmid could be linearized before transformed into *B. subtilis* in order to improve the integration efficiency. Barcodes N21, N22, 5UTR3 and N31 were used between CamR and Idh-HT, AmpR and pMB1, pMB1 and Idh-HF, cpsadh and CamR. All the barcodes and primers used in this section can be found in the paper published by Ma et al., 2019 unless otherwise stated.

*Escherichia coli* strain DH5α was used as the recipient in all cloning experiments. After the plasmids were confirmed by using Sanger sequencing, they were used to transform *B. subtilis* 1A1 following the manufacturer's instruction. The genome-edited *B. subtilis* 1A1 was named as BsADH1. The pHT01-cpsadh harboring *B. subtilis* 1A1 was designated as BsADH2.

1.3 Media and Culture Conditions 1.3.1 *E. coli* DH5α Culture Medium and Growth Conditions

*E. coli* DH5α was cultured aerobically at 37° C. in Luria-Bertani (LB) medium. Ampicillin (100 μg/mL) was added when needed. Agar (15 g/L) was added before the sterilization for preparing LB agar plates.

1.3.2 Induction of Protein Expression in BsADH2

A single colony of BsADH2 was picked from an agar plate with 5 μg/mL of chloramphenicol and inoculated into 10 mL of 2×PY medium (20 g/L of peptone, 10 g/L of yeast extract, and 10 g/L of NaCl, pH 7) with 5 μg/mL of chloramphenicol and aerobically incubated at 37° C. overnight. Overnight grown cell culture was added into 30 mL of fresh 2×PY medium with an initial cell density ($OD_{600}$) of 0.15. Then the cells were incubated at 37° C. with a shaking speed of 225 rpm. Isopropyl β-d-1-thiogalactopyranoside (IPTG) (1 mM) was added when $OD_{600}$ reached 0.7 to 0.8 to induce protein expression. Then the cells were incubated at 37° C./225 rpm unless otherwise stated.

1.3.3 *C. beijerinckii* G117 Culture Media and Growth Conditions

For the anaerobic culture of *C. beijerinckii* G117, a mineral salts medium (termed as anaerobic medium in this study) was adopted with modification (Xin et al. 2016). The medium contained 0.75 g/L of $KH_2PO_4$, 0.75 g/L of $K_2HPO_4$, and 5 g/L of yeast extract. In addition, 1 mL of trace element solution, 1 mL of $Na_2SeO_3$—$Na_2WO_4$ solution, and 10 mg of resazurin were added into 1 L of the medium. Then the medium was flushed with $N_2$ and boiled for 20 minutes. After it was cooled down to 25° C., $Na_2S$, L-cysteine and dithiothreitol were added as reductants (their final concentrations were 0.2 mM, 0.2 mM and 0.5 mM, respectively). After that, $CH_3COONH_4$ and 2-(N-morpholino)ethanesulfonic (MES) were added to final concentrations of 2 g/L and 3.9 g/L respectively. After pH was adjusted to 7 using 100 g/L of NaOH, the medium was dispensed into serum bottles. Then the bottles were sealed with butyl stoppers and autoclaved at 121° C. for 20 minutes.

To prepare the medium without anaerobic pre-treatment (named as aerobic medium in this study), all ingredients were mixed in the same concentrations as the anaerobic medium except the reductants and resazurin were not omitted. The medium was not flushed with $N_2$ during the process. After pH of the medium was adjusted to 7 by 100 g/L of NaOH, the medium was filtered through polyethersulfone (PES) membrane whose pore size was 0.22 μm. Glucose was supplemented upon inoculation.

*C. beijerinckii* G117 from the inventors' laboratory spore stocks was precultured in 50 mL of the anaerobic medium supplemented with 60 g/L of glucose in a 160-mL serum bottle at 37° C./225 rpm for 24 hours. Then the precultured cells were inoculated into the fresh aerobic medium or anaerobic medium with 60 g/L of glucose in an inoculum ratio of 10% and incubated at 37° C./225 rpm unless otherwise stated.

1.3.4 Anaerobic Acetone Reduction by BsADH2 Mono-Culture

BsADH2 was cultivated at 37° C./225 rpm for 8 hours after induction. Then the cell culture was centrifuged at 20,000×g for 10 minutes.

After the supernatant was discarded, the cell pellets were resuspended into 10 mL of the anaerobic medium with 60 g/L of glucose in a 20-mL serum bottle with a butyl stopper and incubated at 37° C./225 rpm. Three grams per liter of acetone was added in the beginning where appropriate. In the control experiment, wild-type *B. subtilis* 1A1 (designated as Bs1A1) was cultivated under the same condition. Samples were taken periodically for analysis.

1.3.5 Co-Culture of BsADH2 and *C. beijerinckii* G117

BsADH2 was cultivated at 37° C./225 rpm for 8 hours after the induction. After that, cell pellets collected from 10 mL of the cell culture were resuspended into 5 mL of the aerobic medium with 60 g/L of glucose in a 20-mL serum bottle with a butyl stopper. After being cultured in the anaerobic medium with 60 g/L of glucose at 37° C./225 rpm for 24 hours, 500 μL of the *C. beijerinckii* G117 cell culture was injected into the aerobic medium with BsADH2 above. Then the co-culture was processed at 37° C./225 rpm. The pH of the aerobic medium was adjusted to 7 using 100 g/L NaOH at 0, $12^{th}$ and $24^{th}$ hour. Samples were taken periodically.

In the control experiment, Bs1A1 was firstly cultured following the same procedure with BsADH2 except that no IPTG was added. After that, Bs1A1 was co-cultured with *C. beijerinckii* G117 following the BsADH2-*C. beijerinckii* G117 co-culture protocol described above.

In the aerobic co-culture experiment in the open system, the co-culture was processed in a 50-mL conical tube with a loosened cap at 37° C. statically. Other procedures were the same as what was described above.

1.4 Determination of Number of Viable BsADH2 Cells in the Co-Culture

Cell culture from different time points was taken. Then 100 μL of cell culture was centrifuged at 20,000×g for 2 minutes. After the supernatant was removed, the cell pellets were washed twice with 1 mL of sterile DI water. Subsequently, 100 μL of sterile deionized (DI) water was used to resuspend the cell pellets. Then the cell suspension was diluted with sterile DI water in series ($10^2$ folds, 104 folds, and $10^6$ folds) to enable accurate counting of colonies. Finally, 50 μL of each suspension was plated on Lysogeny Broth (LB) agar plate and incubated at 37° C. overnight. The number of viable BsADH2 cells was determined by colony counting. Determination of viable Bs1A1 cell number was done following the same procedure as a control.

1.5 Optimization of Process Parameters

*C. beijerinckii* G117 was cultured in 5 mL of the anaerobic medium with 60 g/L of glucose in a 20-mL serum bottle with a butyl stopper at 37° C./225 rpm for 24 hours. After that, cell pellets of the IPTG-induced BsADH2 from 10 mL of the cell culture was inoculated into the *C. beijerinckii* G117 culture. After the pH was adjusted to 7 using 100 g/L of NaOH, the cells were incubated at 37° C./225 rpm. Samples were taken periodically. A control (Bs1A1) was also included.

1.6 Protein Extraction and Analysis

BsADH2 was cultivated at 37° C./225 rpm for 8 hours after induction. Then 10 mL of the cell culture was centrifuged at 20,000×g for 10 minutes. The supernatant was decanted. The cell pellets were frozen at −20° C. for 2 hours. Subsequently, 1 mL of B-PER Complete Reagent (Thermo Scientific) was added to resuspend the cells. After being incubated at room temperature for 15 minutes, the cell lysates were centrifuged at 16,000×g for 20 minutes. The supernatant was used for sodium dodecyl sulfate-polyacrylamide gel electrophoresis (SDS-PAGE) based on the manufacturer's instruction.

In the case of the BsADH1, the cells were cultured in 10 mL of the aerobic medium with 60 g/L of glucose in a 20-mL serum bottle with a butyl stopper. After being incubated at 37° C. for 8 hours, the cell culture was centrifuged at 20,000×g for 10 minutes. Then the cell pellets were frozen at −20° C. for 2 hours and lysed by B-PER. After the cells were lysed, the supernatant was used for SDS-PAGE.

A control (Bs1A1) was also included.

1.7 Analytical Techniques

Cell density was measured by monitoring the optical density (OD) at 600 nm with a visible spectrophotometer (Novaspec II, Pharmacia Biotech, Cambridge, England).

Glucose, lactate, acetate, and butyrate were quantified by High Performance Liquid Chromatography (HPLC) (Agilent Technologies, USA) equipped with a refractive index detector (RID) and variable wavelength detector (VWD) (210 nm). A Bio-Rad Aminex HPX-87H column (300 mm×7.8 mm) was used. Five micromolar of sulfuric acid was used as the mobile phase at the flow rate of 0.7 mL/min.

Butanol, acetone, ethanol, and isopropanol were quantified by gas chromatography (GC, model 7890A; Agilent Technologies, USA) equipped with a Durabond (DB)-WAXetr column (30 m×0.25 mm×0.25 μm, J&W, USA) and flame ionization detector (FID). The oven temperature was initially maintained at 60° C. for 2 mins, increased at 15° C./min to 230° C., and held for 1.7 min. Helium was used as the carrier gas with a column flow rate of 1.5 mL/min (Chua et al. 2013).

2: Anaerobic Isopropyl and Butyl Esters Production *Clostridium*—*Clostridium* Co-Culture System Materials and Methods 2.1 Bacterial Strains and Lipases

*Clostridium beijerinckii* BGS1 used in this study was from a previous study (van den Berg et al., 2013). *Clostridium tyrobutyricum* ATCC 25755 was acquired from Deutsche Sammlung von Mikroorganisem und Zellkulturen (DSMZ) (Braunschweig, Germany).

Lipases used in this study include Lipase immobilized on Immobead 150 from *Rhizopus oryzae* (assigned as Lipase A in this study); Lipase from *Candida* sp. (recombinant, expressed in *Aspergillus niger*, assigned as Lipase B in this study); Lipase from *Rhizopus oryzae* (powder, light brown, ≥30 U/mg, assigned as Lipase C in this study); Lipase from *Candida rugosa* (Type VII, ≥700 unit/mg solid, assigned as Lipase D in this study). All the lipases used were purchased from Sigma-Aldrich PTE LTD.

2.2 Medium and Culture Conditions

A mineral salts medium was used in this study (Xin et al., 2016). The medium contained 0.75 g/L $K_2HPO_4$, 0.75 g/L $KH_2PO_4$, 5 g/L yeast extract. In addition, 1 mL trace element solution, 1 mL $Na_2SeO_3$—$Na_2WO_4$ solution, and 10 mg of resazurin were added into 1 L of the medium. The composition of the trace element solution and $Na_2SeO_3$—$Na_2WO_4$ are listed in Tables 3 and 4. After that, the medium was boiled for 20 minutes under the flushing of $N_2$. Then it was cooled down to 25° C. Subsequently, $Na_2S$, L-cysteine, and DL-dithiothreitol were added to a final concentration of 0.2, 0.2, and 0.5 mM respectively. After that, $CH_3COONH_4$ and 2-(N-morpholino)ethanesulfonic acid were added with final concentrations of 2.0 g/L and 3.9 g/L, respectively. The pH was then adjusted to 7 with 100 g/L NaOH. After that, the medium was dispensed into serum bottles with butyl stoppers. Subsequently, the serum bottles were sealed with aluminum seal crimp caps. Finally, the dispensed medium autoclaved at 121° C. for 20 minutes and cooled down to 25° C. The medium was stored at room temperature before it was used.

TABLE 3

Trace element solution (1 L)

| Chemicals used | Amount ml | Amount g |
|---|---|---|
| HCl (25% solution, w/w) | 10 | — |
| $FeCl_2 \cdot 4H_2O$ | — | 1.5 |
| $CoCl_2 \cdot 6H_2O$ | — | 0.19 |
| $MnCl_2 \cdot 4H_2O$ | — | 0.1 |
| $ZnCl_2$ | — | 0.07 |
| $H_3BO_3$ | — | 0.006 |
| $Na_2MoO_4 \cdot 2H_2O$ | — | 0.036 |
| $NiCl_2 \cdot 6H_2O$ | — | 0.024 |
| $CuCl_2 \cdot 2H_2O$ | — | 0.002 |

TABLE 4

$Na_2SeO_3$—$Na_2WO_4$ Solution (1 L)

| Chemicals used | Amount ml | Amount g |
|---|---|---|
| $Na_2SeO_3 \cdot 5H_2O$ | — | 0.006 |
| $Na_2WO_4 \cdot 2H_2O$ | — | 0.008 |
| NaOH | — | 0.5 |

2.2.1 Culture Conditions of *C. beijerinckii* BGS1 Monoculture

*C. beijerinckii* BGS1 from laboratory spore stocks was precultured in 50 mL of mineral salts medium supplemented with 90 g/L of glucose in a 160-mL serum bottle at 37° C./225 rpm for 24 hours. Then 5 mL of the preculture was inoculated into 45 mL of the defined mineral salts medium with 90 g/L of glucose in a 160-mL serum bottle and cultured at 37° C./225 rpm. The pH was allowed to decrease to 6 with the growth of the cells. After that, pH was adjusted to 6 with 100 g/L NaOH every 12 hours. Samples were taken periodically.

2.2.2 Culture Conditions of *C. beijerinckii* BGS1-*C. tyrobutyricum* ATCC 25755 Co-Culture

*C. beijerinckii* BGS1 from laboratory spore stocks was precultured in 50 mL of mineral salts medium supplemented with 90 g/L of glucose in a 160-mL serum bottle at 37° C./225 rpm for 24 hours.

*C. tyrobutyricum* ATCC 25755 from laboratory spore stock was precultured in 50 mL of mineral salts medium supplemented with 90 g/L of glucose in a 160-mL serum bottle at 37° C./225 rpm for 24 hours.

Five milliliters of *C. beijerinckii* BGS1 preculture was inoculated into 45 mL of the mineral salts medium with 90 g/L of glucose in a 160-mL serum bottle and cultured at 37° C./225 rpm. Then 0.5 mL of the *C. tyrobutyricum* ATCC 25755 preculture was inoculated. The pH was allowed to decrease to 6 with the growth of the cells. After that, pH was adjusted to 6 with 100 g/L NaOH every 12 hours. Samples were taken periodically.

2.3 Lipase Screening

Ten milliliters of an aqueous solution composed of 10 g/L butanol, 5 g/L isopropanol, 10 g/L butyric acid, and 10 g/L acetic acid was prepared and added into a 20-mL serum bottle with a butyl stopper. After 250 U of each lipase was added into different bottles, 5 mL of hexadecane was added as the extractant. The bottles were incubated at 37° C./225 rpm. Samples were taken regularly.

2.4 Production of Esters at Different pH Values

Butanol, isopropanol, butyric acid, and acetic acid were added into a 20-mL serum bottle with a butyl stopper in a final concentration of 10 g/L, 5 g/L, 10 g/L, and 10 g/L respectively to form a 10-mL aqueous solution. After pH was adjusted to 3, 4, 5, and 6 with 100 g/L NaOH, 250 U of Lipase B was added. Five milliliters of hexadecane was added as extractant. The pH was monitored throughout the experiment so that it was constant. 2.5 Esterification from *C. beijerinckii* BGS1 mono-culture and *C. beijerinckii* BGS1-*C. tyrobutyricum* ATCC 25755 co-culture After being cultured for 120 hours, 10 mL of the cell culture from *C. beijerinckii* BGS1 mono-culture or *C. beijerinckii* BGS1-*C. tyrobutyricum* ATCC 25755 co-culture was transferred into a 20-mL serum bottle with a butyl stopper. Then, sodium butyrate was added where appropriate. After pH was adjusted to 3 to 4 with 100 g/L $H_2SO_4$, 250 U of the Lipase B was added. Finally, 5 mL of hexadecane was added as extractant. The reaction was allowed to happen at 37° C./225 rpm. Samples were taken periodically.

2.6 Analytical Methods

Butanol, acetone, isopropanol, and esters were quantified by gas chromatography (GC, model 7890A; Agilent Technologies, USA) equipped with a Durabond (DB)-WAXetr column (30 m×0.25 mmm×0.25 μm, J&W, USA) and flame ionization detector (FID). The oven temperature was initially maintained at 60° C. for 2 min, increased at 15° C./min to 230° C., and held for 1.7 min. Helium was used as carrier gas with a flow rate of 1.5 mL/min (Xin F, et al., 2016).

Glucose, acetate, and butyrate were measured by high-performance liquid chromatography (HPLC, Agilent Technologies, USA) equipped with a refractive index detector (RID) and variable wavelength detector (VWD) (210 nm). The column used was Bio-Rad Aminex HPX-87H column (300 mm×7.8 mm). The mobile phase was 5 mM sulfuric acid and the flow rate was 0.7 mL/min.

As the partition coefficient of butyl butyrate in the hexadecane/aqueous system was reported to be more than 300 (Zhang et al., 2017; van den Berg et al., 2013), the esters in the aqueous phase were neglected in this study. All esters were quantified from the hexadecane layer and the concentrations were divided by 2 (the volume of the aqueous phase was two times that of the hexadecane phase) so that the unit would be in (g of esters)/(L of aqueous phase). For other metabolites such as glucose, acids, and alcohols, they were all quantified from the aqueous samples because their partition coefficients in the hexadecane/aqueous system are relatively low (0.027 for butyrate, 0.043 for butanol) (Zhang et al., 2017).

Example 2

Interaction Between CpSADH-Expressing *B. subtilis* and *C. beijerinckii* G117

Figure 1:
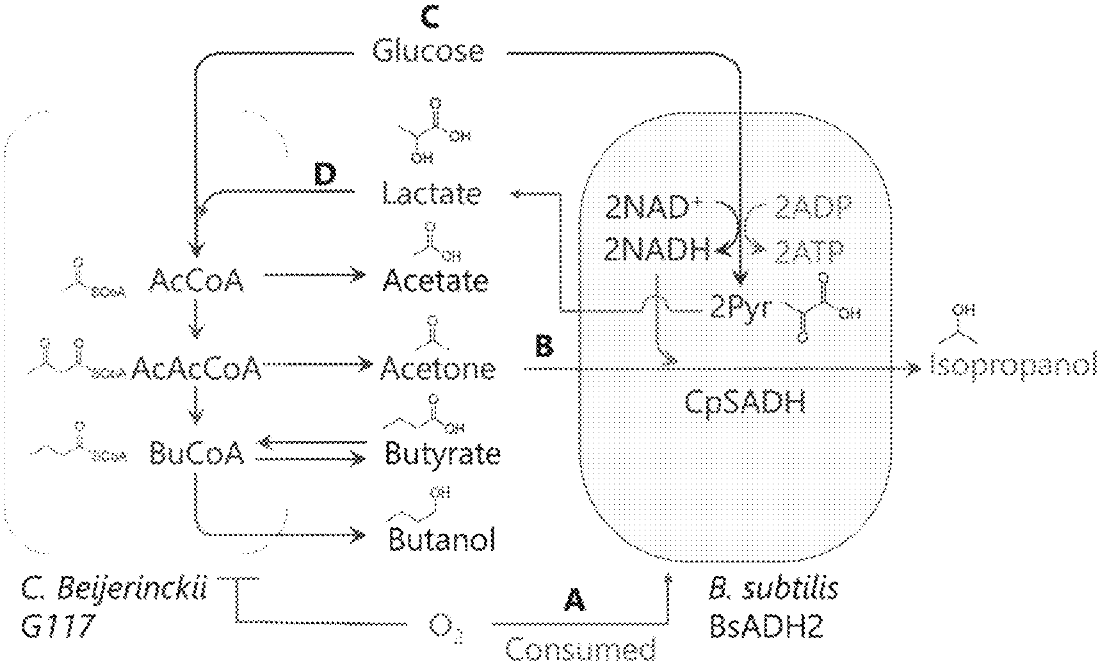
FIG. 1 shows the microbial interactions between the CpSADH-expressing *B. subtilis* (BsADH2) and *C. beijerinckii* G117 in the co-culture. (A) BsADH2 protects *C. beijerinckii* G117 from oxygen. (B) The expression of CpSADH enables BsADH2 to maintain its redox balance by reducing acetone produced by *C. beijerinckii* G117 into isopropanol. (C) BsADH2 and *C. beijerinckii* G117 compete for glucose which is a common carbon source for both strains. (D) lactate produced by BsADH2 was assimilated by *C. beijerinckii* G117. AcCoA: acetyl-CoA. AcAcCoA: acetoacetyl-CoA. BuCoA: butyryl-CoA. Pyr: pyruvate.

When *B. subtilis* BsADH2 was co-cultured with *C. beijerinckii* G117 in the aerobic medium (as defined in Materials and Methods 1.3.5), BsADH2 grew first, which consumed oxygen in the medium. Meanwhile, lactate was also produced by BsADH2 as a product. In this process, glucose was only consumed by BsADH2. After the oxygen was depleted in the peripheral environment, the anaerobic *C. beijerinckii* G117 started to grow under the protection of BsADH2. During the growth of *C. beijerinckii* G117, acetone, butanol, butyrate, and acetate were produced. Meanwhile, the lactate produced by BsADH2 was assimilated by *C. beijerinckii* G117. Acetone was reduced into isopropanol by BsADH2 (FIG. 1). After the oxygen was depleted, glucose was consumed by both BsADH2 and *C. beijerinckii* G117, forming a competitive relationship between the two strains.

Example 3

Expression of CpSADH in *B. subtilis* 1A1

Figure 2:
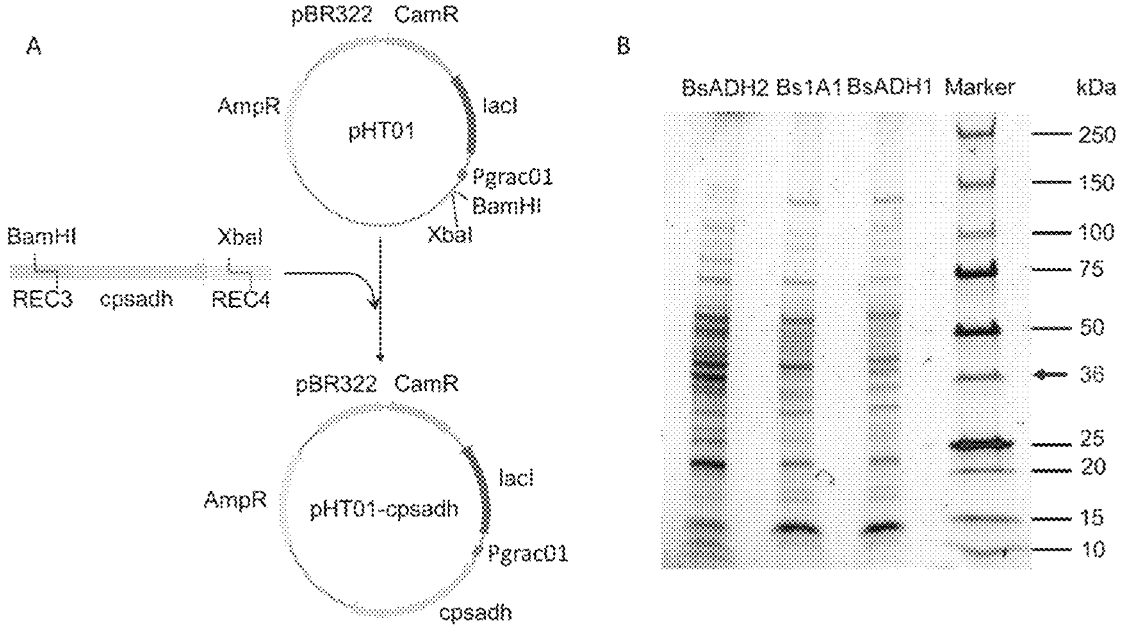
FIG. 2 shows plasmid construction and expression of CpSADH. (A) Construction of the pHT01-cpsadh plasmid. After being barcoded with REC3-F and REC4-R, cpsadh was double-digested by BamHI and XbaI and ligated with the pHT01 plasmid which was also digested by BamHI and XbaI, yielding pHT01-cpsadh. (B) SDS-PAGE analysis of the CpSADH expression in BsADH2, Bs1A1 and BsADH1. A thick band at 36 kDa (molecular mass of CpSADH) was only seen in the lane of BsADH2.

CpSADH has been widely used in biocatalysis research (Liu and Li 2019). To investigate the performance of CpSADH in reducing acetone into isopropanol, the inventors constructed a replicative plasmid pHT01-cpsadh by cloning cpsadh into the pHT01, a *B. subtilis* expression vector (FIG. 2A). An integrative vector pMB1-Idh:operonCm was also constructed as an alternative (FIG. 3). The gene that encodes lactate dehydrogenase (LDH) was chosen as the integration locus because Idh promoter was reported to be able to drive the expression of heterologous genes efficiently under non-aerated conditions (Romero et al. 2007). The inventors hypothesized that the CpSADH could be expressed by the native Idh promoter in the genome-edited strain (named as BsADH1) under the oxygen-limited condition during the co-culture process. These two plasmids were used to transform *B. subtilis* 1A1 separately to compare their performance. After successful insertion of cpsadh into the Idh locus (validated by both colony PCR and Sanger sequencing of PCR products), BsADH1 was cultured in the aerobic medium for 8 hours in a serum bottle with a butyl stopper to mimic the non-aerated condition that is typically used in *Clostridium* culture (Romero et al. 2007). The strain carrying the replicative plasmid (named as BsADH2) and the parental strain *B. subtilis* 1A1 (termed as Bs1A1, used as a control) were cultured in the same medium with IPTG supplemented when appropriate to induce the protein expression. After the protein expression, cells were harvested and sodium dodecyl sulfate-polyacrylamide gel electrophoresis (SDS-PAGE) was conducted to assess the expression level of CpSADH. The lane of BsADH2 showed a thick band at 36 kDa (the molecular weight of CpSADH), which suggested the successful expression of CpSADH (FIG. 2B). By contrast, no target protein was produced by Bs1A1. Surprisingly, there was no target band when BsADH1 was used, indicating that CpSADH was not expressed even though the sequencing result proved that the integration was successful. This was probably due to the complicated working mechanism of the Idh promoter which is beyond the scope of this study. BsADH2 was employed for the rest of the study.

Example 4

Anaerobic Reduction of Acetone by Mono-Culturing BsADH2

After the successful expression of CpSADH, the ability of CpSADH to convert acetone into isopropanol was tested under anaerobic conditions. BsADH2 was cultured at 37° C. in the anaerobic medium supplemented with 60 g/L of glucose and 3 g/L of acetone which mimicked the acetone concentration produced by a typical *Clostridium* culture. BsADH2 was also cultured in the same medium without acetone as a control. Another control experiment with Bs1A1 was also included.

Figure 4:
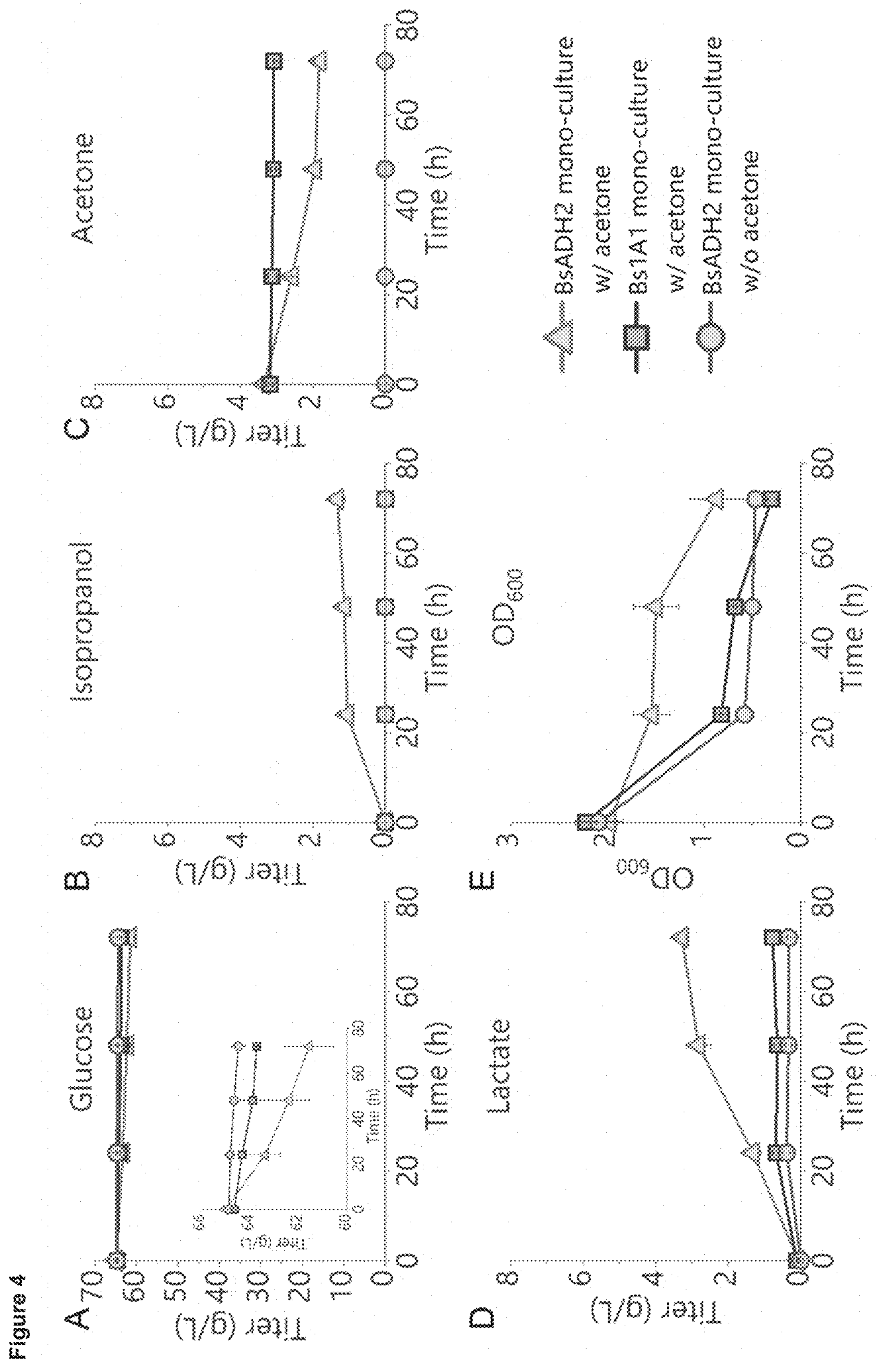
FIG. 4 shows acetone reduction through the anaerobic mono-culture of BsADH2 and Bs1A1. Time profile of (A) glucose, (B) isopropanol, (C) acetone, (D) lactate, and (E) $OD_{600}$ during the fermentation. Isopropanol was only produced when the *B. subtilis* strain expressed CpSADH and acetone was supplemented. Yellow triangles: BsADH2 anaerobically mono-cultured in the anaerobic medium supplemented with 60 g/L glucose and 3 g/L acetone. Blue squares: Bs1A1 anaerobically mono-cultured in the anaerobic medium supplemented with 60 g/L glucose and 3 g/L acetone. Green circles: BsADH2 anaerobically mono-cultured in the anaerobic medium supplemented with 60 g/L glucose only. Error bars indicate standard error (n=3).

In the case of BsADH2 fed with acetone, 1.0 g/L of isopropanol was produced after 24 hours with a productivity of 0.042 g/L/h, together with the production of 1.3 g/L of lactate from 1.6 g/L of consumed glucose (FIGS. 4A, B, and D), indicating the successful conversion of some acetone into isopropanol under the anaerobic condition. In this process, BsADH2 converted glucose to lactate at anaerobic condition to generate ATP. Acetone should have served as an electron acceptor to allow carbon metabolism to be active beyond the pyruvate branch point. Since 1.6 g/L glucose could not provide all the NADH used for both lactate production and acetone reduction under the anaerobic condition, the needed electrons could be derived from further oxidation of glucose beyond pyruvate, which might occur at anaerobic condition in BsADH2 when acetone was used as the electron acceptor. Further cultivating the cells for another 48 hours led to the production of another 0.3 g/L of isopropanol, resulting in a total of 1.3 g/L isopropanol produced (FIG. 4B). Although the conversion rate was only 39.4% and there was still 1.8 g/L of acetone left in the medium (FIG. 4C), this result was comparable with some native isopropanol producers which achieved a conversion rate of 37.2% (Xin et al. 2017). As a comparison, no acetone was reduced when Bs1A1 was cultured anaerobically (FIG. 4C). Interestingly, the lactate titer obtained with Bs1A1 was 0.8 g/L, which was lower than what was produced by BsADH2 (3.3 g/L). This phenomenon may be due to glucose uptake being enhanced when acetone was reduced into isopropanol by CpSADH, which was absent in Bs1A1. When BsADH2 was cultured in the same medium without acetone, only 0.3 g/L of lactate was produced, suggesting that expressing CpSADH alone was insufficient to trigger the phenotype. Finally, carbon recovery of BsADH2 mono-cultured with acetone, Bs1A1 mono-cultured with acetone, and BsADH2 mono-cultured without acetone reached 0.933, 0.736, and 0.865 respectively (Table 5).

TABLE 5

Carbon recovery calculation

| | BsADH2 w/acetone | Bs1A1 w/acetone | BsADH2 w/o acetone |
|---|---|---|---|
| $\Delta m_{glucose}$ | 3.44 | 0.91 | 0.37 |
| $\Delta C_{glucose}$ | 0.114667 | 0.030333 | 0.012333 |
| $\Delta m_{lactate}$ | 3.21 | 0.67 | 0.32 |
| $\Delta C_{lactate}$ | 0.107 | 0.022333 | 0.010667 |
| $CR_{glucose}$ | 0.933 | 0.736 | 0.865 |

Carbon Recovery Calculation of *B. subtilis* Anaerobic Mono-Culture

Assumptions

1. Cell population did not increase.
2. Isopropanol was all reduced from acetone.

Consumed Carbons from Glucose (mol/L):

$$\Delta C_{glucose} = \frac{\Delta m_{glucose}}{180} \times 6$$

Recovered Carbons from Lactate (mol/L):

$$\Delta C_{lactate} = \frac{\Delta m_{lactate}}{90} \times 3$$

Carbon Recovery for Glucose:

$$CR_{glucose} = \frac{\Delta C_{lactate}}{\Delta C_{glucose}}$$

Noteworthily, although the production of lactate kept increasing until the end of the culture, the production of isopropanol in the mono-culture of BsADH2 nearly stopped after 24 hours (FIGS. 4B and D). A possible reason is that the reduction of pyruvate to lactate and reduction of acetone to isopropanol are both sinks of electrons, the latter of which might not be needed by the cells after the production of lactate started.

Figure 5:
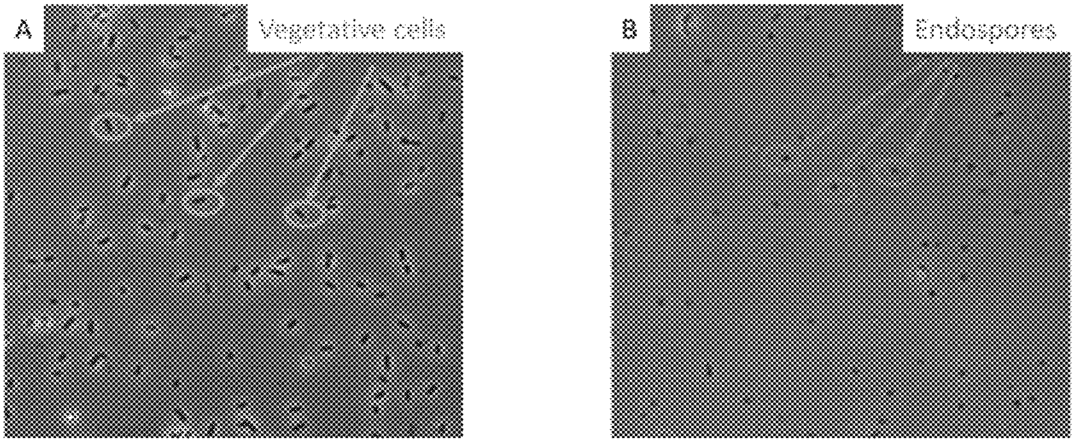
FIG. 5 shows the microscopic images of cells from the 48 hours' anaerobic mono-culture supplemented with 60 g/L of glucose and 3 g/L acetone of (A) BsADH2 and (B) Bs1A1, which were taken by using a phase-contrast microscope with 40× magnification. The cells in the yellow circles are vegetative cells. The cells in the green circles are endospores.

*B. subtilis* was reported to be able to grow anaerobically in the presence of glucose/nitrite or glucose/pyruvate (Romero et al. 2007). In this experiment, Bs1A1 could only generate lactate to maintain the redox balance of glycolysis under the anaerobic condition when glucose was fed as the only carbon source. The lactate production cannot sink all electrons liberated from decarboxylation of pyruvate through pyruvate dehydrogenase, so C2 metabolites may not be obtained anaerobically. The inventors have observed that Bs1A1 became round and smaller under the anaerobic condition (FIG. 5), and there was a sharp decline of optical density from 2.2 to 0.7 after being cultured anaerobically for 48 hours (FIG. 4E). As a comparison, the optical density of BsADH2 cultured in the medium with acetone decreased much slower from 2.0 to 1.5 within 48 hours. By using acetone as the electron acceptor to sink the electrons, pyruvate in BsADH2 may be decarboxylated to produce the C2 metabolites under the anaerobic redox balance constraint, which led to a more active cellular metabolism when BsADH2 was cultured anaerobically. This hypothesis was also supported by the rapid decline of $OD_{600}$ when BsADH2 was anaerobically cultured without acetone as the electron acceptor (FIG. 4E). Being able to reduce acetone anaerobically is vital in the co-culture process because *B. subtilis* needs to maintain an active metabolism for isopropanol production after the oxygen was depleted in the peripheral environment.

In an attempt to improve the production of isopropanol, a few inoculum sizes were tested, but the isopropanol production was not improved (FIG. 6A-B), suggesting that the rate-limiting factor was not the amount of CpSADH.

Figure 6:
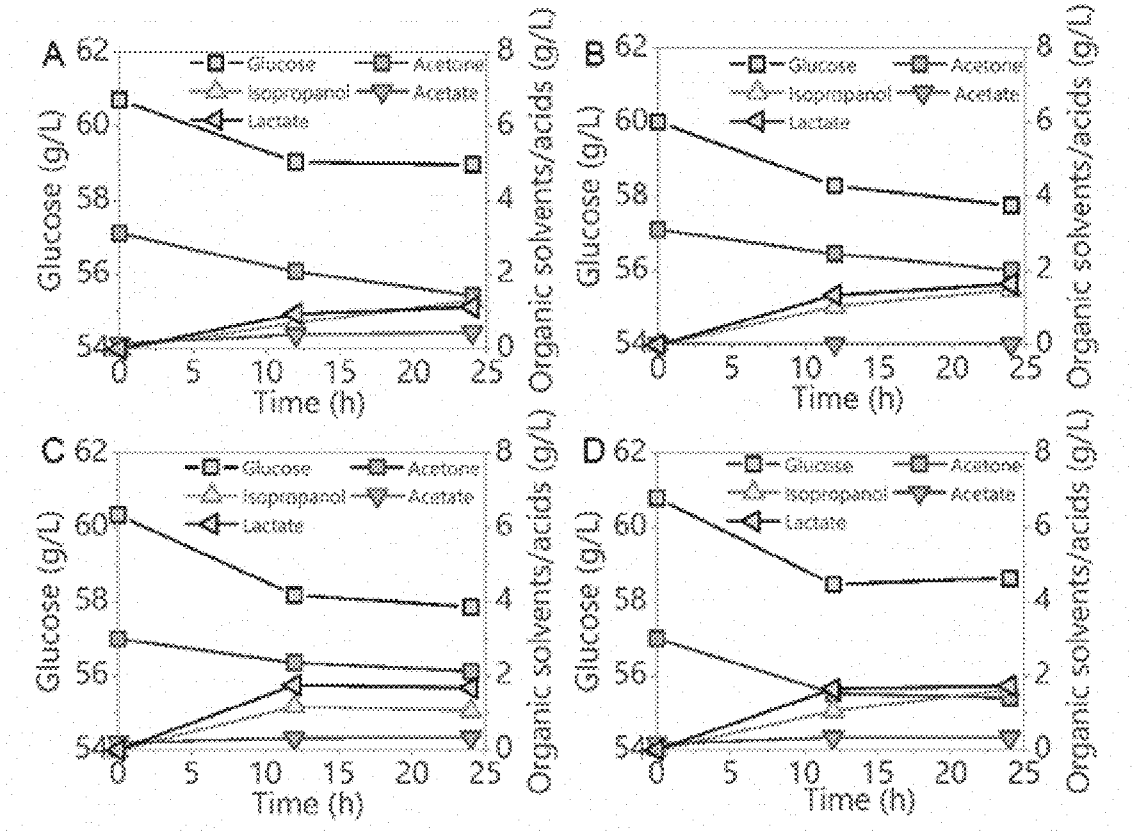
FIG. 6 shows the profiles of anaerobic mono-culture of BsADH2 in the anaerobic medium with 60 g/L of glucose and 3 g/l of acetone. (A) Cells were induced at 37° C. for 8 hours before inoculation. Cell pellets from 15 mL of induced cell culture was inoculated into 5 mL of the anaerobic medium. (B) Cells were induced at 37° C. for 8 hours before inoculation. Cell pellets from 20 mL of induced cell culture was inoculated into 5 mL of the anaerobic medium. (C) Cells were induced at 25° C. overnight before inoculation. Cell pellets from 10 mL of induced cell culture was inoculated into 5 mL of the anaerobic medium. (D) Cells were induced at 30° C. overnight before inoculation. Cell pellets from 10 mL of induced cell culture was inoculated into 5 mL of the anaerobic medium.

Culture temperature was reported to be critical in the expression of recombinant protein (Wang et al. 2009). Reducing growth temperature was used as a strategy to improve the expression of the recombinant protein by improving protein folding (Zhou et al. 2012; Mhlmann et al. 2017). Therefore, the cells were cultured at 25° C., 30° C., or 37° C. after induction to investigate the effect of temperature on the expression of CpSADH. However, induction at different temperatures did not substantially affect the anaerobic acetone reduction, further suggesting that the rate-limiting factor was not the activity of CpSADH (FIG. 6C-D).

Example 5

Switching AB to ABI Fermentation by Co-Culturing *C. beijerinckii* G117 and BsADH2 in the Aerobic Medium in Closed and Open Systems After the inventors confirmed that BsADH2 can reduce acetone into isopropanol under the anaerobic condition, the inventors further tested if the strain could reduce acetone produced by *Clostridium* when they were co-cultured. *C. beijerinckii* G117 was chosen as the *Clostridium* strain in the co-culture experiment because it does not produce ethanol, an undesired by-product (Chua et al. 2013). Besides, this strain can also tolerate 5 μg/mL of chloramphenicol, which was needed to maintain the replicative plasmid in BsADH2. In addition, *C. beijerinckii* G117 produces negligible amount of acids, which made pH adjustment easier during the fermentation (Chua et al. 2013).

To test whether *C. beijerinckii* G117 can grow in the aerobic medium (which did not undergo any anaerobic treatment to remove oxygen) with the help of BsADH2, the two strains were inoculated into the aerobic medium at the beginning of the fermentation. As the induction of protein expression in BsADH2 in the co-culture system might fail due to the anaerobic condition (the promoter was only tested under the aerobic condition), the inventors decided to inoculate high concentrations of induced and aerobically grown BsADH2 cells in the co-culture (initial cell density of BsADH2=4 based on $OD_{600}$). To alleviate the effect of lactate production by BsADH2 on pH which might lead to slower growth of *C. beijerinckii* G117, pH was periodically adjusted back to 7 with 100 g/L of NaOH during the first 24 hours (Chua et al. 2013). A control (*C. beijerinckii* G117-Bs1A1 co-culture) going through the same procedure was also included.

Figure 7:
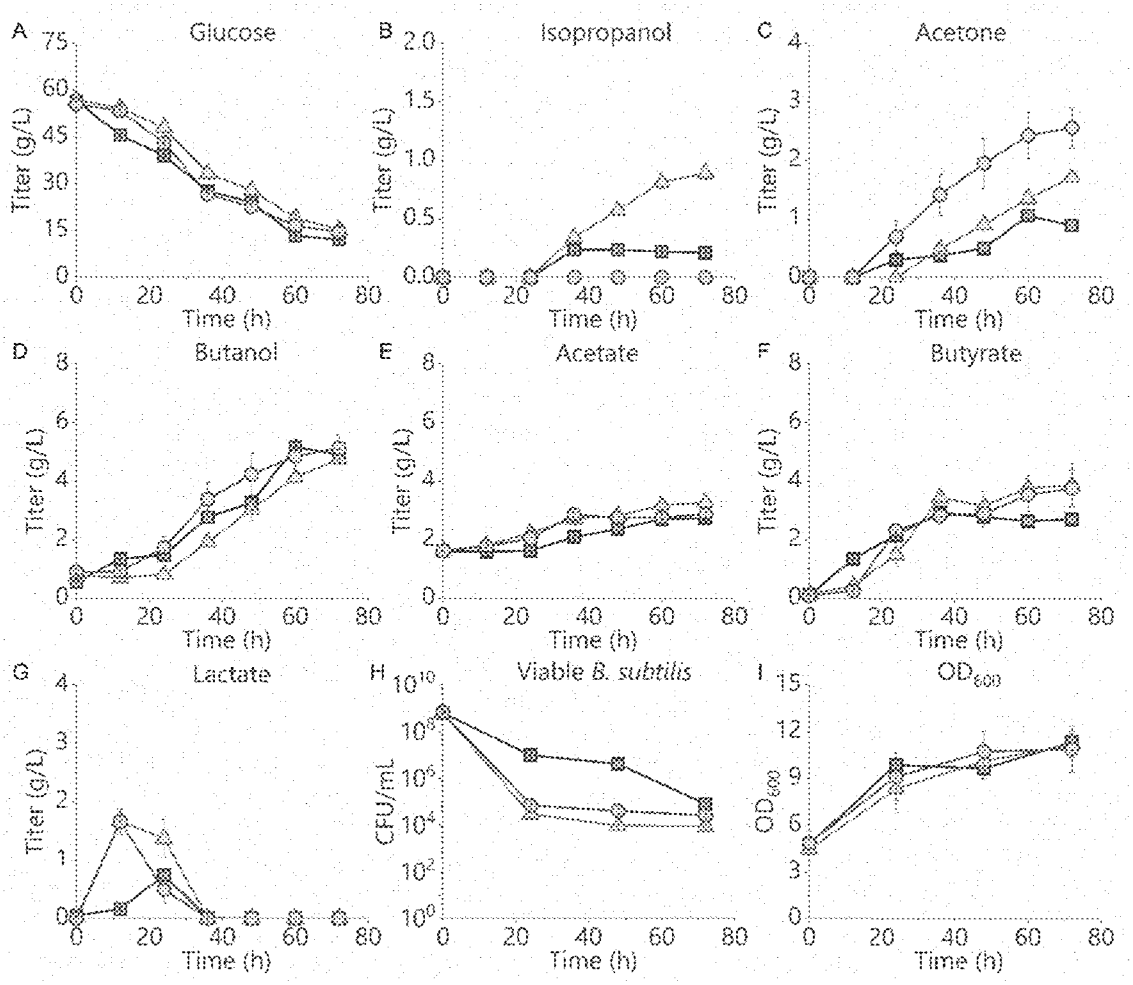
FIG. 7 shows fermentation results of BsADH2-*C. beijerinckii* G117 and Bs1A1-*C. beijerinckii* G117 co-cultures. BsADH2 produced isopropanol when co-cultured with *C. beijerinckii* G117, even when oxygen continuously diffused to the system. A-I: Time profiles of (A) glucose, (B) isopropanol, (c) acetone, (D) butanol, (E) acetate, (F) butyrate, (G) lactate, (H) number of viable *B. subtilis* cells, and (1) $OD_{600}$ during the co-cultures. J: yields of products. Yields were calculated based on obtained products (mol) per mole of consumed glucose. Alcohols: isopropanol and butanol. Acids: acetate and butyrate. Total: alcohols and acids. Blue squares: BsADH2-*C. beijerinckii* G117 co-culture in the aerobic medium supplemented with 60 g/L of glucose in 50-mL conical tubes (open system). Yellow triangles: BsADH2-*C. beijerinckii* G117 co-culture in the aerobic medium supplemented with 60 g/L of glucose in serum bottles (closed system). Green circles: Bs1A1-*C. beijerinckii* G117 co-culture in the aerobic medium supplemented with 60 g/L of glucose in serum bottles (closed system). Error bars indicate standard error (n=3).
Figure 8:
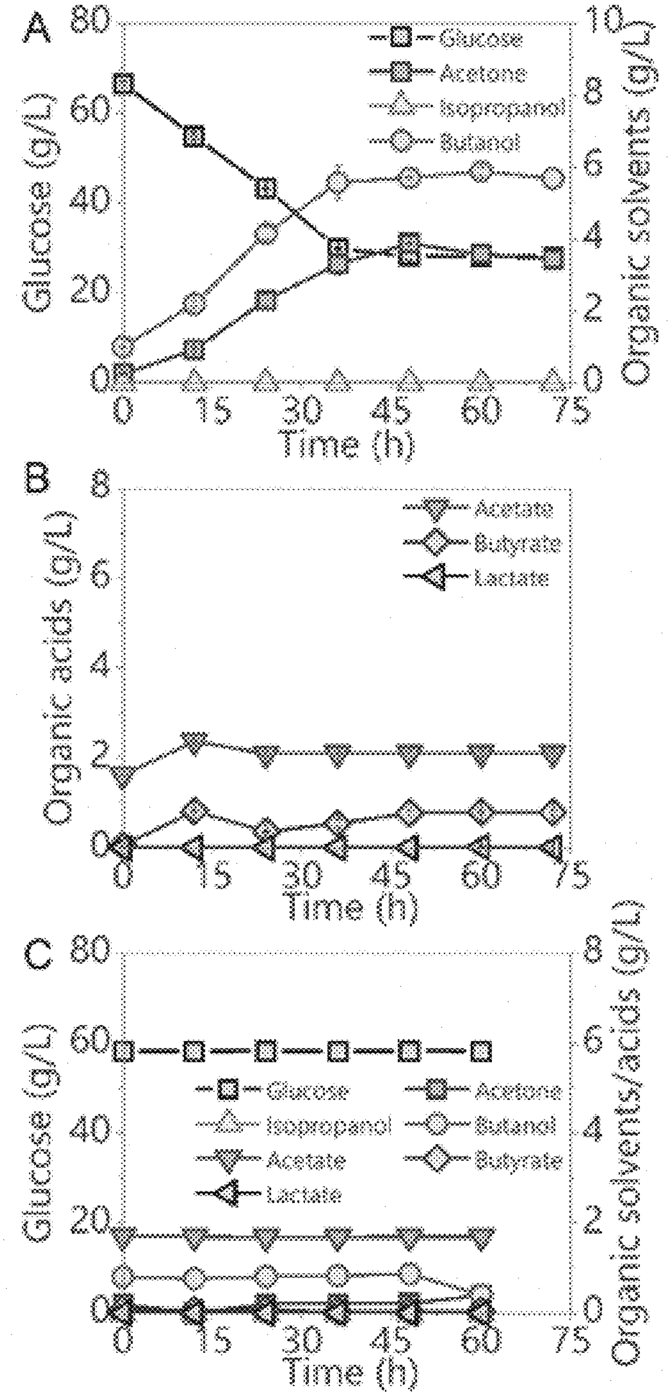
FIG. 8 shows the batch fermentation profiles of *C. beijerinckii* G117. (A) Glucose and organic solvents concentration of anaerobic mono-culture of *C. beijerinckii* G117. (B) Organic acids concentration of anaerobic mono-culture of *C. beijerinckii* G117. (C) Glucose, organic solvents and acids concentration of *C. beijerinckii* G117 mono-culture in the aerobic medium.

After the lag phase, *C. beijerinckii* G117 grew rapidly as evidenced by the production of butyrate in the co-culture with BsADH2 (FIG. 7F). After the brief acidogenic phase which produced acetate and butyrate, the cells entered the solventogenic phase from the $24^{th}$ hour, when butanol and acetone were produced from glucose at 0.081 g/L/h and 0.047 g/L/h respectively (FIGS. 7A, C, D, E and F). During this process, isopropanol was produced along with acetone. The isopropanol concentration stopped increasing after 72 hours, and reached a final titer of 0.9 g/L, together with 4.8 g/L of butanol, 1.7 g/L of acetone, and 3.9 g/L of butyrate (FIGS. 7B, C, D, and F). During the last 48 hours, the productivity of isopropanol was 0.019 g/L/h which was 20% of that of butanol (FIG. 7B). Further cultivating the cells for another 48 hours did not lead to an increase in the butanol and acetone concentrations (data not shown). Finally, the yield of alcohols (butanol and isopropanol) with respect to glucose achieved 0.346 (mol/mol), which was 14% higher than that from the Bs1A1-*C. beijerinckii* G117 co-culture, due to the reduction of acetone (FIG. 7J). The solvent production performance of the co-culture system was comparable with that of the *C. beijerinckii* G117 mono-culture which produced 5.7 g/L of butanol and 3.4 g/L of acetone under the anaerobic condition (FIG. 8A). As expected, no isopropanol was produced in the anaerobic mono-culture of *C. beijerinckii* G117 (FIG. 8A). Notably, less butyrate was produced in the anaerobic mono-culture of *C. beijerinckii* G117 than what was produced in the co-culture system, which may be due to the adjustment of pH during the co-culture process (FIG. 8B). In the case of Bs1A1 (control) co-cultured with *C. beijerinckii* G117, 5.1 g/L of butanol, 2.6 g/L of acetone, and 3.8 g/L of butyrate were produced (FIGS. 7C, D, and F), without the production of isopropanol. This result demonstrated that Bs1A1 was not able to reduce the acetone produced by *C. beijerinckii* G117. When *C. beijerinckii* G117 was cultured in the aerobic medium without *B. subtilis* 1A1 (BsADH2 and Bs1A1), it neither produced organic acids/alcohols nor showed cell growth (FIG. 8C). This observation was consistent with the results of other studies (Wu et al. 2016). An interesting phenomenon is that when *B. subtilis* 1A1 (BsADH2 and Bs1A1) was co-cultured with *C. beijerinckii* G117, lactate was produced in the first 12 hours. After reaching a plateau at 2 g/L at the $12^{th}$ h, lactate was re-assimilated (FIG. 7G). In comparison to the anaerobic mono-culture of *B. subtilis* 1A1 (BsADH2 and Bs1A1) in which lactate concentration did not decrease, the re-assimilation observed in the co-culture should be attributed to *C. beijerinckii* G117 because some *C. beijerinckii* strains have been reported to utilize lactate to produce butanol and butyrate (Hou et al. 2017; Detman et al. 2019). The re-assimilation of lactate, which was the primary by-product of the *B. subtilis* cells, reduced the waste of carbon source. Moreover, the lactate concentration in the Bs1A1-*C. beijerinckii* G117 co-culture decreased more rapidly than that in the BsADH2-*C. beijerinckii* G117 co-culture although the two systems shared similar *C. beijerinckii* G117 growth, suggesting that the BsADH2 may have produced more lactate during the fermentation, which was consistent with what was observed in the anaerobic mono-culture of BsADH2.

To better understand the interactions between the two strains in the co-culture, the number of viable *B. subtilis* (BsADH2 and Bs1A1) cells was determined by counting number of colonies that grew on the aerobically incubated LB agar plates—*C. beijerinckii* G117 cannot grow aerobically.

Although BsADH2-*C. beijerinckii* G117 co-culture produced isopropanol, it did not contain a larger number of viable *B. subtilis* cells than Bs1A1-*C. beijerinckii* G117 co-culture during the fermentation (FIG. 7H). This was probably due to the absence of acetone during the early stage of the fermentation. After the anaerobic environment was achieved, *C. beijerinckii* G117 experienced a lag phase during which acetone was not produced. However, oxygen was depleted rapidly by BsADH2, which led to the decline of viable BsADH2 cell number due to the lack of electron acceptor (acetone). This was also supported by the rapid decrease of $OD_{600}$ when BsADH2 was anaerobically mono-cultured in the absence of acetone (FIG. 4E). As a result, only a part of BsADH2 population survived to produce isopropanol during the later stage of the co-culture, which might also contribute to the lower productivity of isopropanol in comparison with the anaerobic acetone reduction by BsADH2. By contrast, $OD_{600}$ of the both Bs1A1-*C. beijerinckii* G117 and BsADH2-*C. beijerinckii* G117 co-culture increased over time, which should be due to the growth of *C. beijerinckii* G117 (FIG. 7I).

Conducting the experiments in the medium without any anaerobic pre-treatment in serum bottles simplified the experimental procedure. However, the production of gas including $H_2$ and $CO_2$ by *C. beijerinckii* G117 in a closed system remained a problem. Gas needed to be released regularly to avoid pressure built-up inside the closed system. Therefore, it would be desirable if the co-culture could be maintained in an open system. To achieve this target, the inventors further co-cultured the cells in a 50-mL conical tube whose cap was loosened. This condition was defined in this study as an aerobic condition because oxygen (air) continuously diffused into the system.

The aerobic co-culture of *C. beijerinckii* G117 and BsADH2 in the open system showed similar performance in some aspects as the co-culture in the aerobic medium in the serum bottle. After 72 hours of cultivation, 4.9 g/L of butanol and 2.7 g/L of butyrate were produced (FIGS. 7D and F). This result suggested that the dissolved oxygen level in the medium under this real aerobic condition was zero or very close to zero, which was achieved by the action of BsADH2. Notably, only 0.9 g/L of acetone and 0.2 g/L isopropanol were obtained, leading to an isopropanol/acetone ratio of 0.22 which was less than half of that obtained from the co-culture in the closed system (FIGS. 7B and C). This may be due to the evaporation of acetone and isopropanol which have lower boiling points than butanol. Besides, the respiration of BsADH2 in the open system may also compete with acetone reduction in oxidizing NADH. Additionally, the number of viable BsADH2 cells showed a slower decrease in the open system (FIG. 7H), suggesting that BsADH2 maintained a more active metabolism when oxygen was more accessible. On the other hand, BsADH2 still could protect *C. beijerinckii* G117 from oxygen, leading to the normal growth of *C. beijerinckii* G117 (FIG. 7I).

Compared with other studies only using *Bacillus* as an oxygen consumer, the inventors successfully established a mutually dependent relationship consisting of protection and feeding between *C. beijerinckii* and *B. subtilis* (Wu et al. 2016). *B. subtilis* (BsADH2) protected *C. beijerinckii* G117 from the exposure of 02 and fed lactate to *C. beijerinckii* G117. In return, *C. beijerinckii* G117 produced acetone for the *B. subtilis* (BsADH2) to better maintain its redox balance. In addition, results from co-culture in the open system proved that the co-culture process the inventors developed here showed the potential as a safer, easier, and more economical way to switch the anaerobic AB fermentation into the aerobic ABI fermentation which does not require the tedious and costly anaerobic pre-treatment and troublesome gas-releasing practice.

Example 6

Optimization of Process Parameters

As the titer of isopropanol produced in the co-culture system still needed to be improved, the inventors further inoculated BsADH2 into the 24-hour anaerobic cell culture of *C. beijerinckii* G117 so that there would be more acetone available when BsADH2 was added.

Figure 9:
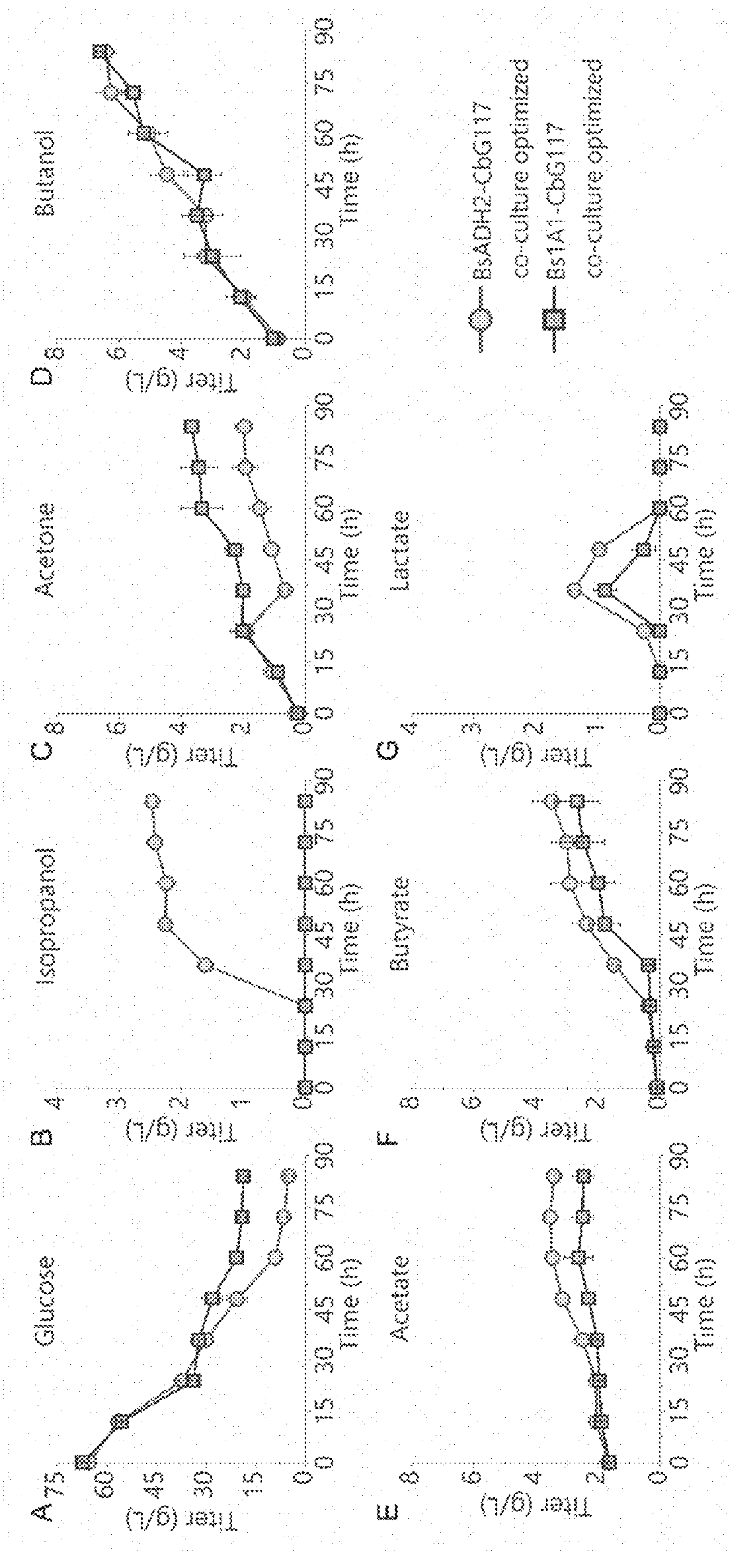
FIG. 9 shows the optimization of process parameters in the co-culture. The optimization was done by adding *B. subtilis* BsADH2 or Bs1A1 into the *C. beijerinckii* G117 culture that had been incubated for 24 hours. The moment that *C. beijerinckii* G117 mono-culture started was designated as 0 h. Time profiles of (A) glucose, (B) isopropanol, (C) acetone, (D) butanol, (E) acetate, (F) butyrate, and (G) lactate during the fermentation are shown in the figure. Green circles: optimized BsADH2-*C. beijerinckii* G117 co-culture. Blue squares: optimized Bs1A1-*C. beijerinckii* G117 co-culture. Error bars indicate standard error (n=3).

After the addition of BsADH2, 1.3 g/L of acetone was reduced into isopropanol within 12 hours, and that was more than what was reduced in the aerobic co-culture system (FIG. 9C). Acetate and butyrate were also produced (FIGS. 9E and F). Further cultivating the cells for another 12 hours led to the production of another 0.7 g/L of isopropanol from glucose (FIGS. 9A, B, C, and D). Afterward, no more isopropanol was produced. This is consistent with the result of the anaerobic acetone reduction experiment by BsADH2 mono-culture that isopropanol was only produced during the first 24 hours. Overall, 6.4 g/L of butanol and 3.5 g/L of butyrate were produced after 72 hours, which was comparable with what were produced by the anaerobic mono-culture of *C. beijerinckii* G117. Meanwhile, 2.0 g/L of acetone and 2.5 g/L of isopropanol were also obtained (FIGS. 9B and C). In comparison, no isopropanol was produced when Bs1A1 was added into the *C. beijerinckii* G117 culture, with similar titers of butanol and butyrate produced (FIGS. 9B, D, and F).

Example 7

Mechanism of the Reaction and Selection of Lipases

Figure 10:
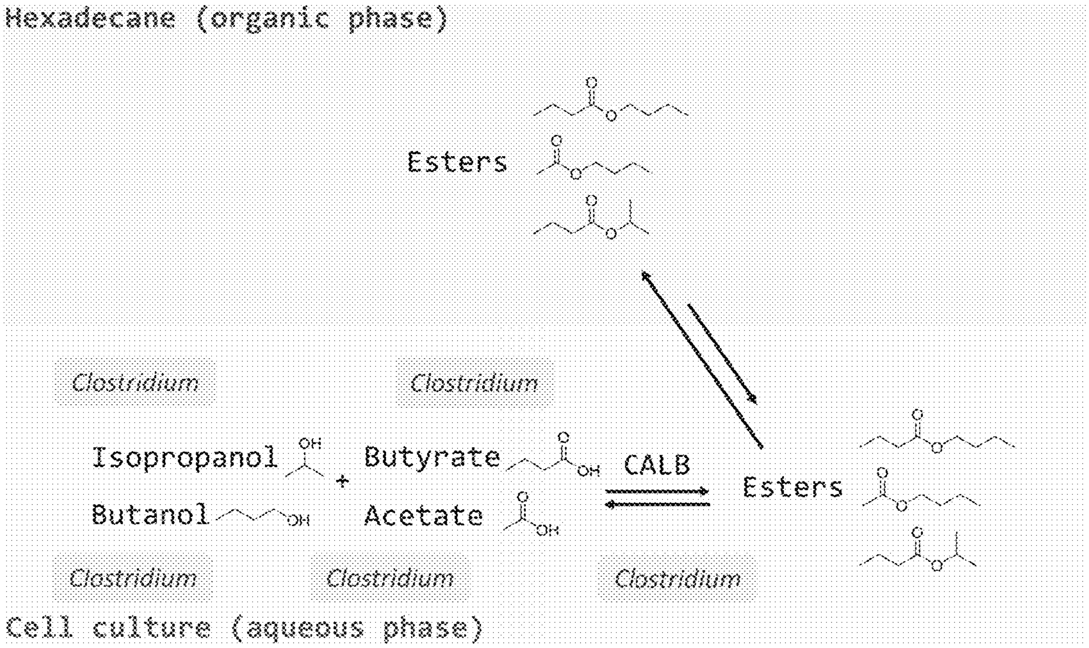
FIG. 10 shows the mechanism of the biphasic esterification. CALB: *Candida antarctica* lipase B.

Adding lipase to the culture medium of *Clostridium* fermentation can condense the acids and alcohols in the medium into esters, which can be extracted by an organic phase if it is present (FIG. 10). This process will drive the esterification reaction forward until an equilibrium is achieved.

Organic extractants such as kerosene, Bio-OSR, and hexadecane have been used for the extraction of butyl-butyrate from the aqueous phase (Xin et al., 2018). Considering the partition coefficient, biocompatibility, and availability (Zhang Z T, Taylor S, Wang Y 2017), hexadecane was chosen as the extractant in this study.

To identify a suitable lipase in this application, four commercially available lipases—Lipase from *Rhizopus oryzae* (immobilized on Immobead 150, termed as Lipase A in this study), Lipase from *Candida* sp. (recombinant, expressed in *Aspergillus niger*, termed as Lipase B in this study), Lipase from *Rhizopus oryzae* (powder, light brown, ≥30 U/mg, termed as Lipase C in this study), and Lipase from *Candida rugosa* (Type VII, ≥700 unit/mg solid, termed as Lipase D in this study)—were evaluated by using a mixture of 10 g/L butanol, 5 g/L isopropanol, 10 g/L butyric acid, and 10 g/L acetic acid as substrates.

Figure 11:
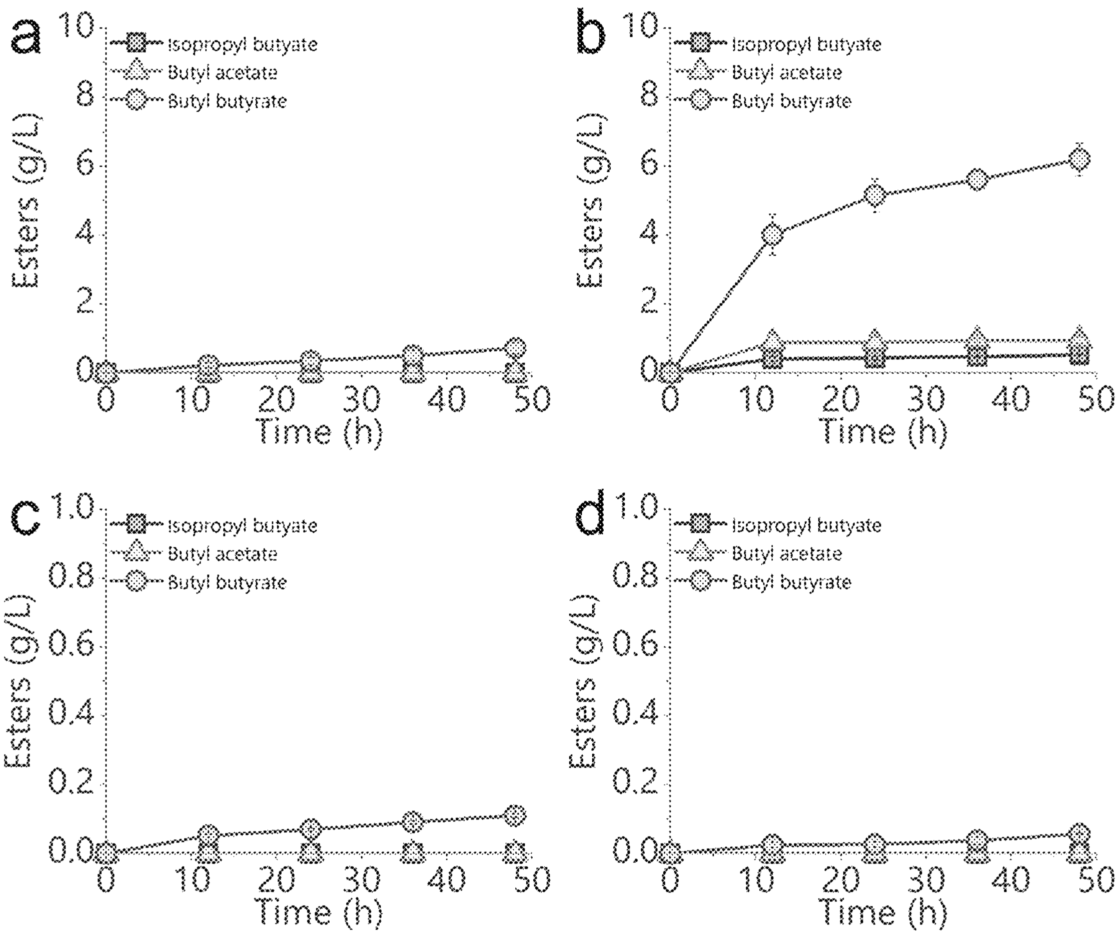
FIG. 11 shows the selection of lipases. Esterification of butanol, isopropanol, butyric acid, and acetic acid by using four lipases. (a) Lipase A (lipase, immobilized on Immobead 150 from *Rhizopus oryzae*). (b) Lipase B (lipase from *Candida* sp. [recombinant, expressed in *Aspergillus niger*]). (c) Lipase C (lipase from *Rhizopus oryzae* [powder, light brown, ≥30 U/mg]). (d) Lipase D (lipase from *Candida rugosa* [Type VII, ≥700 unit/mg solid]). Error bars, mean±s.e. in all graphs (some error bars are smaller than the plot symbols). There are three replicates for each data point.

Among the four lipases, Lipase B was the best in terms of ester productivity and titer. After 12 hours' reaction, 0.4 g/L of isopropyl butyrate was produced, along with 0.9 g/L of butyl acetate and 4.0 g/L of butyl butyrate (FIG. 11B). Further allowing the reaction to proceed another 36 hours led to the production of another 0.1 g/L of isopropyl butyrate, 0.1 g/L of butyl acetate, and 2.2 g/L of butyl butyrate. As a comparison, no isopropyl butyrate was produced when other lipases were used. When Lipase A was added, 0.7 g/L of butyl butyrate was produced within 48 hours (FIG. 11A). In the case of Lipase C and D, 0.1 g/L and 0.06 g/L of butyl butyrate were produced, respectively, as the only product within 48 hours (FIGS. 11C and D). Lipase B was selected in the subsequent esterification experiments based on the results obtained.

Example 8

Effect of pH During the Esterification Stage

As an important factor in the esterification process, pH was empirically optimized. The pKa of butyric acid at room temperature is 4.82, while the pKa of acetic acid is 4.76. Lower pH will lead to more undissociated acids in the reaction system, which promotes the production of esters (only undissociated acids can participate in esterification reaction). However, lipase could be denatured if the pH is too low, leading to poor ester production (Ng C H, Yang K L 2016).

Figure 12:
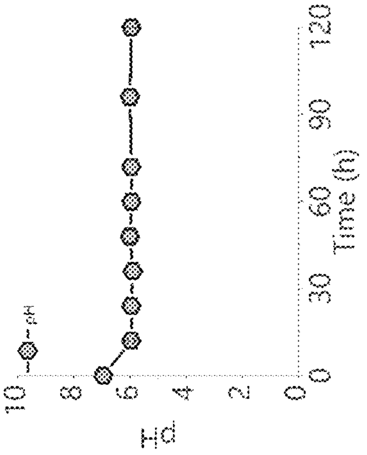
FIG. 12 shows the time profile of pH during the *C. beijerinckii* BGS1 mono-culture.

Lipases were added into the mixture of 10 g/L butanol, 5 g/L isopropanol, 10 g/L butyric acid, and 10 g/L acetic acid with different pH. During the fermentation of *C. beijerinckii* BGS1, pH usually decreases from 7 to 6 due to the production of butyrate and acetate. After that, pH remains at around 6 till the end of the fermentation (FIG. 12). Therefore, pH 6 was initially selected for producing esters from the acids/alcohols mixture. However, almost no esters were produced when pH 6 was used during the esterification stage, suggesting that lower pH was needed to facilitate the esterification (FIG. 14A). Failing to produce esters at pH 6 suggests that esters cannot be produced by using this lipase during the fermentation. When pH was decreased to 5, isopropyl butyrate was produced at a titer of 0.2 g/L, accompanied by the production of 0.3 g/L of butyl acetate and 2.4 g/L of butyl butyrate within 12 hours (FIG. 14A), confirming that a lower pH can promote the production of esters. The inventors further decreased pH to 4, which led to the production of more than doubled the amount of esters (0.5 g/L of isopropyl butyrate, 0.7 g/L of butyl acetate, and 5.3 g/L of butyl butyrate) within 12 hours. No substantial improvement was achieved in terms of ester titer when pH was further decreased to 3, suggesting that a pH of 3 to 4 was good for producing esters. Therefore, pH was maintained at 3 to 4 in the following esterification reactions. Noteworthily, equilibrium was achieved after 12 hours in all the cases (FIG. 15), suggesting a high efficiency of Lipase B in catalyzing the esterification reactions.

Example 9

Use of Exogenously Added Butyrate to Increase Ester Production

Figure 13:
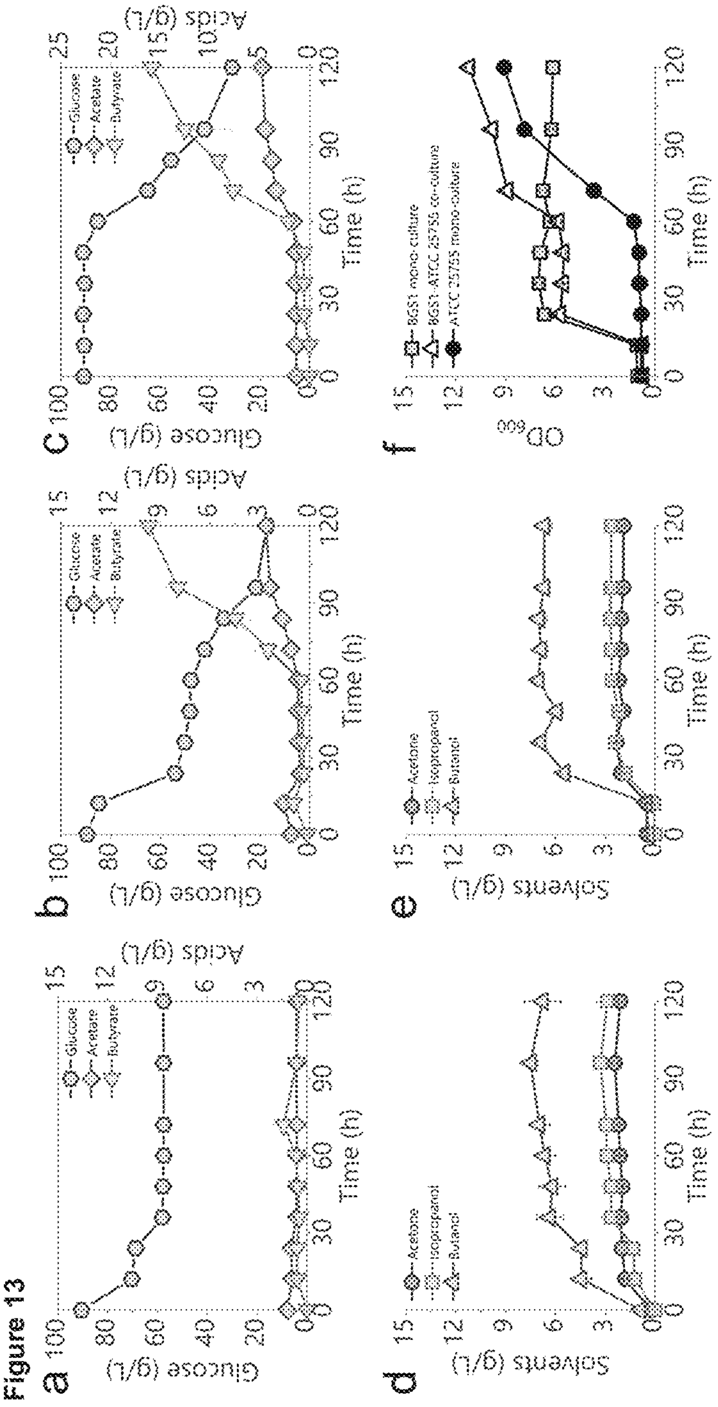
FIG. 13 shows the results of a method using *C. tyrobutyricum* ATCC 25755 to provide butyrate in a co-culture for ester production. (a) Time profile of glucose and organic acids concentration in the mono-culture of *C. beijerinckii* BGS1. (b) Time profile of glucose and organic acids concentration in the co-culture of *C. beijerinckii* BGS1 and *C.*

During the fermentation of *C. beijerinckii* BGS1, 6.8 g/L of butanol and 2.9 g/L of isopropanol were produced. However, only 0.8 g/L of butyrate was produced, which is much lower than the stoichiometric quantity that is needed to completely utilize the alcohols (FIGS. 13A and C). As a result, butyrate was supplemented exogenously so that a better acids/alcohols ratio could be achieved. In theory, a high concentration of butyrate can also drive the equilibrium of the reaction to the ester side. However, ester production might be inhibited if the butyrate concentration is too high due to the enzyme inactivation or inhibitory action of the substrate (Devi et al., 2017). To optimize butyrate concentration, sodium butyrate was added into the 120-hour culture of *C. beijerinckii* BGS1 to achieve the following final concentration of butyrate (not considering the butyrate produced by the cells): 10.0 g/L, 15.0 g/L, 20.0 g/L, and 40.0 g/L.

Supplementing 10 g/L of butyrate led to the production of 0.4 g/L of isopropyl butyrate within 12 hours, along with the production of 0.1 g/L of butyl acetate and 6.4 g/L of butyl butyrate (FIG. 14B). As a comparison, no esters were produced without the addition of butyrate. This is consistent with the results from other studies that adding exogenous butyrate is necessary to produce esters from the fermentation product of solventogenic *Clostridium* (Xin et al., 2016). To increase the titers of esters, more butyrate was added. Increasing the butyrate concentration to 40.0 g/L led to the production of 1.3 g/L of isopropyl butyrate and 11.0 g/L of butyl butyrate. At this condition, 83% of the produced butanol and 21% of the produced isopropanol were converted into esters. The titer of butyl butyrate showed a slower increase when butyrate concentration increased from 10 g/L to 40 g/L, indicating that the titers of esters might be mainly limited by the concentration of alcohols when the concentration of butyrate exceeded 10 g/L.

Example 10

Co-Culture of *C. beijerinckii* BGS1 and *C. tyrobutyricum* ATCC 25755

Although adding butyrate exogenously increased the titers of esters, the operation will increase the complexity of the fermentation process and incur a higher substrate cost.

As an acidogenic strain, *C. tyrobutyricum* ATCC 25755 is well known for its good ability of producing butyrate (Liu X, Zhu Y, Yang S T (2006)). In these experiments, 15.9 g/L of butyrate was produced by *C. tyrobutyricum* ATCC 25755 mono-culture within 120 hours, without the production of solvents (FIG. 13C). As a comparison, *C. beijerinckii* BGS1 produces mainly solvents at pH 6 (FIG. 13A, D). Therefore, the inventors adopted a co-culture strategy that utilized the different characteristics of these two strains at pH 6 to produce the solvents and more butyrate, so that the titers of esters could be increased during the esterification stage without adding butyrate.

When *C. beijerinckii* BGS1 was co-cultured with *C. tyrobutyricum* ATCC 25755, 6.9 g/L of butanol and 2.4 g/L of isopropanol were produced within 36 hours (FIG. 13E). After a 36-hour lag, butyrate started to be produced with a productivity of 0.15 g/L/h, leading to continuous consumption of glucose. Finally, 9.7 g/L of butyrate was produced by the co-culture system (FIG. 13B). A discrepancy of butyrate titer with the *C. tyrobutyricum* ATCC 25755 mono-culture was observed, which was probably due to the toxicity of solvents produced by *C. beijerinckii* BGS1 (FIG. 13C). On the contrary, a negligible amount of butyrate was produced by the mono-culture of *C. beijerinckii* BGS1 (FIG. 13A). Compared with the co-culture, mono-culture of *C. beijerinckii* BGS1 led to a similar production of butanol and isopropanol (6.8 g/L and 2.9 g/L, respectively) (FIG. 13D). Considering that there were two different strains from two different species in this co-culture system and the solvent tolerance of the two species might differ, the difference in the fermentation performance between the co-culture and mono-culture might be explained by solvent inhibition or toxicity. While the amounts of solvents produced by *C. beijerinckii* BGS1 was inhibitory/toxic to *C. beijerinckii* BGS1 itself, *C. tyrobutyricum* ATCC 25755 might have tolerated the solvents and hence grew in the presence of those solvents, leading to continued consumption of glucose. This explanation is supported by the results from another study which proved that *C. tyrobutyricum* can tolerate up to 2.0% (v/v) butanol while *C. beijerinckii* was completely inhibited (Yu M, et al., (2011)). The production of butanol and isopropanol in the first 36 hours should be from *C. beijerinckii* BGS1 in the co-culture, because *C. tyrobutyricum* ATCC 25755 was not known to produce the solvents. From the $60^{th}$ hour, *C. tyrobutyricum* ATCC 25755 started to grow, leading to the production of butyrate, based on the profile of $OD_{600}$ (FIG. 13F). The cell density of *C. beijerinckii* BGS1 stopped increasing after 24 hours in the mono-culture. However, the cell density in the co-culture started to increase again from the $60^{th}$ hour, along with the rapid production of butyrate, which is a typical feature of *C. tyrobutyricum* (FIG. 13C). As a more direct measurement of cell growth of these two strains, expressing an anaerobic fluorescent protein in either *C. tyrobutyricum* ATCC 25755 or *C. beijerinckii* BGS1 and differentiating them under a fluorescence microscope might be helpful in the future. In addition, metabolic engineering of *C. tyrobutyricum* ATCC 25755 and *C. beijerinckii* BGS1 may also help to further convert the remaining acetone into isopropanol. This might be achieved by expressing a secondary alcohol dehydrogenase in either of the strains, which has been proven to be feasible in *C. acetobutylicum* (Lee et al., 2012).

These results suggest that by co-culturing *C. beijerinckii* BGS1 and *C. tyrobutyricum* ATCC 25755, more butyrate could be produced without sacrificing the production of alcohols.

Following the co-culture, the inventors further conducted the esterification reaction by using the fermentation product from *C. beijerinckii* BGS1 mono-culture and *C. beijerinckii* BGS1-*C. tyrobutyricum* ATCC 25755 co-culture.

During the esterification stage, 5.1 g/L of butyl butyrate was produced within 12 hours from the fermentation product of the co-culture (FIG. 16A). Moreover, 0.2 g/L of butyl acetate and 0.2 g/L of isopropyl butyrate was also produced. The titers of esters were similar to those from the experiment in which 10 g/L of butyrate was added into the fermentation product of *C. beijerinckii* BGS1. As a comparison, there was 0.5 g/L of butyl butyrate produced as the sole product from the fermentation product of the *C. beijerinckii* BGS1 mono-culture (FIG. 16B). These results suggest that the introduction of the acidogenic *C. tyrobutyricum* ATCC 25755 improved the production of esters due to the production of more butyrate.

This appears to be the first study reporting the production of both isopropyl butyrate and butyl butyrate from the fermentation product of *Clostridium.*

By adopting this strategy, esters could be produced in descent titers without the addition of exogenous butyrate, representing a more cost-effective way to produce esters from the fermentation product of *Clostridium*. Compared with the strategy in which butyrate-producing strain and alcohols producing strain were cultured separately and then mixed to produce esters, this co-culture strategy might be more advantageous because dilution of the reactants could be avoided, which may lead to high ester titers (FIG. 14B). However, given that commercial lipase was used in this study and its cost could be a concern, further investigation on alleviating or avoiding the usage of commercial lipase is needed. This might be achieved by expressing lipase or alcohol acyltransferase in *Clostridium* in the future (Xin et al., 2016; Noh et al., 2019).

Example 11

Co-Culture of *C. beijerinckii* BGS1 and *C. acetobutylicum* ATCC 824 to Produce Short-Chain Fatty Acid Esters By using the *Bacillus-Clostridium* co-culture strategy (EXAMPLES 1.1; 2-6), acetone was successfully reduced into isopropanol. However, the titer of isopropanol produced was relatively insufficient to produce esters compared to some native IBE-producing *Clostridium*. Therefore, to achieve higher titer of esters and simplify the co-culture system, *C. beijerinckii* BGS1 was used as the isopropanol producer in the production of esters. As an IBE-producing strain, *C. beijerinckii* BGS1 was reported to be able to produced 10.21 g/L butanol and 3.41 g/L isopropanol (Zhang et al., 2018). However, it barely produces butyrate during the fermentation, which raises the requirement of supplementing exogenous butyrate during esterification. To alleviate the addition of butyrate, another strain *C. acetobutylicum* ATCC 824 was introduced to be co-cultured with *C. beijerinckii* BGS1. At pH 6, *C. acetobutylicum* ATCC 824 is in the acidogenic phase, with butyrate and acetate as the main products. *C. beijerinckii* BGS1 is solventogenic at the same pH, with isopropanol and butanol as the main products. Utilizing this difference, *C. beijerinckii* BGS1 and *C. acetobutylicum* ATCC 824 were co-cultured anaerobically at 37° C./225 rpm, with pH maintained at 6.

After 48 hours, 3.2 g/L of butyrate was produced by the co-culture system, along with 7.5 g/L of butanol. In comparison, only 0.6 g/L of butyrate was produced when *C. beijerinckii* BGS1 was mono-cultured (FIG. 17). Further co-culturing the two strains for another 72 hours did not lead to the production of more butyrate (FIG. 17). Noteworthily, the butanol titer increased to 11.8 g/L from the $48^{th}$ hour to the $72^{nd}$ hour, due to the existence of *C. acetobutylicum* ATCC 824. These results suggest that the introduction of *C. acetobutylicum* ATCC 824 increased the titer of butyrate.

To further test the effect of the coculture strategy on the production of esters, a co-culture of *C. beijerinckii* BGS1 and *C. acetobutylicum* ATCC 824, and a mono-culture of *C. beijerinckii* BGS1 were incubated for 120 hours and then subjected to lipase for esterification (FIG. 18).

After the addition of Lipase B, 0.5 g/L of isopropyl butyrate, 1.9 g/L of butyl butyrate and 0.8 g/L of butyl acetate were produced from the co-culture system, whereby the butyl acetate was due to the production of acetate by *C. acetobutylicum* ATCC 824. In comparison, there was only 0.2 g/L of isopropyl butyrate produced from the mono-culture of *C. beijerinckii* BGS1. No other esters were produced. These results suggested that by co-culturing *C. acetobutylicum* ATCC 824 and *C. beijerinckii* BGS1, the titers of ester could be improved.

SUMMARY

The present invention is a new approach to improve the *Clostridium* fermentation.

In one aspect the invention achieves the production of butanol and isopropanol by introducing an aerobe that can be easily genetically modified. The co-culture system utilizes a composition or combination comprising an acetone-butanol-ethanol (ABE)-producing *Clostridium* strain and a genetically engineered *B. subtilis* strain that expresses a secondary alcohol dehydrogenase to successfully shift the anaerobic AB fermentation into an aerobic ABI fermentation. Nevertheless, improvement of the enzymatic activity may be achieved by either engineering the CpSADH used in the Examples, or evaluating more secondary alcohol dehydrogenases (sADH). Further, more strains from the genus of *Clostridium* may also be tested in order to improve the titer of products.

The co-culture of *Clostridium* and *Bacillus* alleviated the production of undesired acetone and avoided the costly anaerobic pre-treatment.

To further convert the isopropanol and butanol into high value-added short chain fatty acid esters without the addition of butyrate, a *Clostridium-Clostridium* co-culture system was developed. In another aspect the invention achieves the production of butyrate, isopropanol and butanol by utilizing a composition or combination comprising a first isopropanol- and butanol-producing *Clostridium* strain and a second butyrate-producing *Clostridium* strain.

Esters may be produced from the products of the fermentation by the addition of lipase. Lipase from *Candida* sp. was found to be the most effective of those tested herein for both the *Clostridium—Bacillus* co-culture and the *Clostridium—Clostridium* co-culture systems.

However, the addition of commercial lipases to produce esters from the products of fermentation may be expensive in a scaled-up commercial production. Therefore, it would be desired if esters could be produced by co-culturing a *Clostridium* strain with a lipase- and secondary alcohol dehydrogenase-expressing *B. subtilis*. In this case, *B. subtilis* would provide respiratory protection for *Clostridium* to initiate the ABE fermentation. Meanwhile, *B. subtilis* would maintain its active cellular metabolism to produce lipase by reducing acetone into isopropanol. As a result, isopropanol, butanol, butyrate, and acetate can be further converted into more valuable esters by the lipase. These esters can be easily extracted in situ by the utilization of extractant. *B. subtilis* genetic engineering is much easier and faster than the *Clostridium* counterpart

REFERENCES

Brault G, Shareck F, Hurtubise Y, et al (2014) Short-chain flavor ester synthesis in organic media by an *E. coli* whole-cell biocatalyst expressing a newly characterized heterologous lipase. PLoS One 9. <doi.org/10.1371/journal.pone.0091872>

Chua T K, Liang D W, Qi C, Yang K L, He J (2013) Characterization of a butanol-acetone-producing *Clostridium* strain and identification of its solventogenic genes. Bioresour Technol 135:372-378. <doi.org/10.1016/j.biortech.2012.08.085>

Detman A, Mielecki D, Chojnacka A, Salamon A, Blaszczyk M K, Sikora A (2019) Cell factories converting lactate and acetate to butyrate: *Clostridium butyricum* and microbial communities from dark fermentation bioreactors. Microb Cell Fact 18:1-12. <doi.org/10.1186/s12934-019-1085-1>

Devi N A, Radhika G B, Bhargavi R J (2017) Lipase catalyzed transesterification of ethyl butyrate synthesis in n-hexane—a kinetic study. J Food Sci Technol 54:2871-2877. https://doi.org/10.1007/si3197-017-2725-2

Dusséaux S, Croux C, Soucaille P, Meynial-Salles I (2013) Metabolic engineering of *Clostridium acetobutylicum* ATCC 824 for the high-yield production of a biofuel composed of an isopropanol/butanol/ethanol mixture. Metab Eng 18:1-8. <doi.org/10.1016/j.ymben.2013.03.003>

Dwidar M, Kim S, Jeon B S, Um Y, Mitchell R J, Sang B I (2013) Co-culturing a novel *Bacillus* strain with *Clostridium tyrobutyricum* ATCC 25755 to produce butyric acid from sucrose. Biotechnol Biofuels 6:1. <doi.org/10.1186/1754-6834-6-35>

Hou X, From N, Angelidaki I, Huijgen W J J, Bjerre A B (2017) Butanol fermentation of the brown seaweed *Laminaria digitata* by *Clostridium beijerinckii* DSM-6422. Bioresour Technol 238:16-21. <doi.org/10.1016/j.biortech.2017.04.035>

Jiang Y, Xu C, Dong F, Yang Y, Jiang W, Yang S (2009) Disruption of the acetoacetate decarboxylase gene in solvent-producing *Clostridium acetobutylicum* increases the butanol ratio. Metab Eng 11:284-291. <doi.org/10.1016/j.ymben.2009.06.002>

Joseph R C, Kim N M, Sandoval N R (2018) Recent developments of the synthetic biology toolkit for *Clostridium*. Front Microbiol 9:1-13. <doi.org/10.3389/fmicb.2018.00154>

Kirk O, Christensen M W (2002) Lipases from *Candida antarctica*: Unique biocatalysts from a unique origin. Org Process Res Dev 6:446-451. <doi.org/10.1021/op0200165>

Kiyoshi, K., Furukawa, M., Seyama, T., Kadokura, T., Nakazato, A., Nakayama, S., 2015. Butanol production from alkali-pretreated rice straw by co-culture of *Clostridium thermocellum* and *Clostridium saccharoperbutylacetonicum*. Bioresour. Technol. 186, 325-328. <doi.org/10.1016/j.biortech.2015.03.061>

Lee J, Jang Y S, Choi S J, Im J A, Song H, Cho J H, Seung D Y, Terry Papoutsakis E, Bennett G N, Lee S Y (2012) Metabolic engineering of *Clostridium acetobutylicum* ATCC 824 for isopropanol-butanol-ethanol fermentation. Appl Environ Microbiol 78:1416-1423. <doi.org/10.1128/AEM.06382-11>

Lee S Y, Park J H, Jang S H, Nielsen L K, Kim J, Jung K S (2008) Fermentative butanol production by clostridia. Biotechnol Bioeng 101:209-228. <doi.org/10.1002/bit.22003>

Lehmann D, Hönicke D, Ehrenreich A, Schmidt M, Weuster-Botz D, Bahl H, Lutke-Eversloh T (2012) Modifying the product pattern of *Clostridium acetobutylicum*: Physiological effects of disrupting the acetate and acetone formation pathways. Appl Microbiol Biotechnol 94:743-754. <doi.org/10.1007/s00253-011-3852-8>

Li L, Ai H, Zhang S, Li S, Liang Z, Wu Z Q, Yang S T, Wang J F (2013) Enhanced butanol production by coculture of *Clostridium beijerinckii* and *Clostridium tyrobutyricum*. *Bioresour Technol* 143:397-404. <doi.org/10.1016/j.biortech.2013.06.023>

Liu J, Li Z (2019) Enhancing cofactor recycling in the bioconversion of racemic alcohols to chiral amines with alcohol dehydrogenase and amine dehydrogenase by coupling cells and cell-free system. Biotechnol Bioeng 116:536-542. <doi.org/10.1002/bit.26896>

Li, Q., Guo, C., Liu, C. Z., 2014. Dynamic microwave-assisted alkali pretreatment of cornstalk to enhance hydrogen production via co-culture fermentation of *Clostridium thermocellum* and *Clostridium thermosaccharolyticum*. Biomass and Bioenergy 64, 220-229. <doi.org/10.1016/j.biombioe.2014.03.053>

Liu X, Zhu Y, Yang S T (2006) Butyric acid and hydrogen production by *Clostridium tyrobutyricum* ATCC 25755 and mutants. Enzyme Microb Technol 38:521-528. <doi.org/10.1016/j.enzmictec.2005.07.008>

Ma X, Liang H, Cui X, Liu Y, Lu H, Ning W, Poon N Y, Ho B, Zhou K (2019) A standard for near-scarless plasmid construction using reusable DNA parts. Nat Commun 10:1-12. <doi.org/10.1038/s41467-019-11263-0>

Mi S, Gu C, Wu P, Liu H, Yan X, Li D, Tang X, Duan X, Wang G, Zhang J (2018) Improvement of butanol production by the development and co-culture of *C. acetobutylicum* TSH1 and *B. cereus* TSH2. Appl Microbiol Biotechnol 102:6753-6763. <doi.org/10.1007/s00253-018-9151-x>

Mühlmann M, Forsten E, Noack S, Büchs J (2017) Optimizing recombinant protein expression via automated induction profiling in microtiter plates at different temperatures. Microb Cell Fact 16:1-12. <doi.org/10.1186/s12934-017-0832-4>

Ng C H, Yang K L (2016) Lipase in biphasic alginate beads as a biocatalyst for esterification of butyric acid and butanol in aqueous media. Enzyme Microb Technol 82:173-179. <doi.org/10.1016/j.enzmictec.2015.10.005>

Noh H J, Woo J E, Lee S Y, Jang Y S (2018) Metabolic engineering of *Clostridium acetobutylicum* for the production of butyl butyrate. Appl Microbiol Biotechnol 102:8319-8327. <doi.org/10.1007/s00253-018-9267-z>

Oliva-Rodríguez A G, Quintero J, Medina-Morales M A, Morales-Martinez T K, Rodríguez-De la Garza J A, Moreno-Dávila M, Aroca G, Rios González LJ (2019) *Clostridium* strain selection for co-culture with *Bacillus subtilis* for butanol production from agave hydrolysates. Bioresour Technol 275:410-415. <doi.org/10.1016/j.biortech.2018.12.085>

Rassadin V G, Likhterova N M, Slavin V N, Zharov A V (2006) Problems in production of high-octane, unleaded automotive gasolines. Chem Technol fuels oils 42:235-242

Rodriguez G M, Tashiro Y, Atsumi S (2014) Expanding ester biosynthesis in *Escherichia coli*. Nat Chem Biol 10:259-265. <doi.org/10.1038/nchembio.1476>

Romero S, Merino E, Bolívar F, Gosset G, Martinez A (2007) Metabolic engineering of *Bacillus subtilis* for ethanol production: Lactate dehydrogenase plays a key role in fermentative metabolism. Appl Environ Microbiol 73:5190-5198. <doi.org/10.1128/AEM.00625-07>

Rude M A, Schirmer A (2009) New microbial fuels: a biotech perspective. Curr Opin Microbiol 12:274-281. <doi.org/10.1016/j.mib.2009.04.004>

Sillers R, Al-Hinai M A, Papoutsakis E T (2009) Aldehyde-alcohol dehydrogenase and/or thiolase overexpression coupled with CoA transferase downregulation lead to higher alcohol titers and selectivity in *Clostridium acetobutylicum* fermentations. Biotechnol Bioeng 102:38-49. <doi.org/10.1002/bit.22058>

Stergiou P Y, Foukis A, Filippou M, et al (2013) Advances in lipase-catalyzed esterification reactions. Biotechnol Adv 31:1846-1859. <doi.org/10.1016/j.biotechadv.2013.08.006>

Survase S A, Jurgens G, Van Heiningen A, Granström T (2011) Continuous production of isopropanol and butanol using *Clostridium beijerinckii* DSM 6423. Appl Microbiol Biotechnol 91:1305-1313. <doi.org/10.1007/s00253-011-3322-3>

Tran H T M, Cheirsilp B, Hodgson B, Umsakul K (2010) Potential use of *Bacillus subtilis* in a co-culture with *Clostridium butylicum* for acetone-butanol-ethanol production from cassava starch. Biochem Eng J 48:260-267. <doi.org/10.1016/j.bej.2009.11.001> van den Berg C, Heeres AS, van der Wielen L A M, Straathof A J J (2013) Simultaneous clostridial fermentation, lipase-catalyzed esterification, and ester extraction to enrich diesel with butyl butyrate. Biotechnol Bioeng 110:137-142. <doi.org/10.1002/bit.24618>

Wang Y, Wang Z, Xu Q, Du G, Hua Z, Liu L, Li J, Chen J (2009) Lowering induction temperature for enhanced production of polygalacturonate lyase in recombinant *Pichia pastoris. Process Biochem* 44:949-954. <doi.org/10.1016/j.procbio.2009.04.019>

Wu P, Wang G, Wang G, Borresen B T, Liu H, Zhang J (2016) Butanol production under microaerobic conditions with a symbiotic system of *Clostridium acetobutylicum* and *Bacillus cereus*. Microb Cell Fact 15:1-11. <doi.org/10.1186/s12934-016-0412-z>

Xin F, Basu A, Yang K L, He J (2016) Strategies for production of butanol and butyl-butyrate through lipase-catalyzed esterification. Bioresour Technol 202:214-219. <doi.org/10.1016/j.biortech.2015.11.068>

Xin F, Chen T, Jiang Y, Dong W, Zhang W, Zhang M, Wu H, Ma J, Jiang M (2017) Strategies for improved isopropanol-butanol production by a *Clostridium* strain from glucose and hemicellulose through consolidated bioprocessing. Biotechnol Biofuels 10:1-13. <doi.org/10.1186/s13068-017-0805-1>

Xin F, Dong W, Jiang Y, et al (2018) Recent advances on conversion and co-production of acetone-butanol-ethanol into high value-added bioproducts. Crit Rev Biotechnol 38:529-540. <doi.org/10.1080/07388551.2017.1376309>

Xin F, He J (2013) Characterization of a thermostable xylanase from a newly isolated *Kluyvera* species and its application for biobutanol production. Bioresour Technol 135:309-315. <doi.org/10.1016/j.biortech.2012.10.002>

Youn S H, Lee K M, Kim K Y, Lee S M, Woo H M, Um Y (2016) Effective isopropanol-butanol (IB) fermentation with high butanol content using a newly isolated *Clostridium* sp. A1424. Biotechnol Biofuels 9:1-16. <doi.org/10.1186/s13068-016-0650-7>

Yu M, Zhang Y, Tang I C, Yang S T (2011) Metabolic engineering of *Clostridium tyrobutyricum* for n-butanol production. Metab Eng 13:373-382. <doi.org/10.1016/j.ymben.2011.04.002>

Zhang C, Li T, He J (2018) Characterization and genome analysis of a butanol-isopropanol-producing *Clostridium beijerinckii* strain BGS1 06 Biological Sciences 0605 Microbiology 06 Biological Sciences 0604 Genetics. Biotechnol Biofuels 11:1-11. <doi.org/10.1186/s13068-018-1274-x>

Zhang Z T, Taylor S, Wang Y (2017) In situ esterification and extractive fermentation for butyl butyrate production with *Clostridium tyrobutyricum*. Biotechnol Bioeng 114:1428-1437. <doi.org/10.1002/bit.26289>

Zhou K, Zou R, Stephanopoulos G, Too H P (2012) Enhancing solubility of deoxyxylulose phosphate pathway enzymes for microbial isoprenoid production. Microb Cell Fact 11:1-8. <doi.org/10.1186/1475-2859-11-148>

The invention claimed is:

1. A composition for the production of butanol and isopropanol, comprising an acetone-butanol-ethanol (ABE)-producing *Clostridium* strain and a genetically engineered *B. subtilis* strain, wherein said genetically engineered *B. subtilis* strain has been transformed by at least one polynucleotide molecule;

the at least one polynucleotide molecule comprising a secondary alcohol dehydrogenase gene operably linked to at least one promoter.

2. The composition of claim 1, wherein the *Clostridium* strain is *C. beijerinckii* G117 deposited according to ATCC Accession number PTA-121569.

3. The composition of claim 1, wherein the secondary alcohol dehydrogenase gene is a *Candida parapsilosis* secondary alcohol dehydrogenase (cpsadh) gene comprising the polynucleotide sequence set forth in SEQ ID NO: 1.

4. The composition of claim 1, wherein the secondary alcohol dehydrogenase gene comprises a polynucleotide sequence having at least 80% sequence identity to the polynucleotide sequence set forth in SEQ ID NO: 1 and encoding the amino acid sequence set forth in SEQ ID NO: 10.

5. The composition of claim 1, wherein the said genetically engineered *B. subtilis* strain has been transformed by at least one polynucleotide molecule to co-express a secondary alcohol dehydrogenase and a lipase.

6. A method of producing butanol and isopropanol in a co-culture, comprising the steps:

a) co-culturing an acetone-butanol-ethanol (ABE)-producing *Clostridium* strain with a genetically engineered *B. subtilis* strain in a medium under conditions for ABE fermentation, wherein the medium has not undergone anaerobic treatment, and b) supplementing the medium with glucose, wherein said genetically engineered *B. subtilis* strain has been transformed by at least one polynucleotide molecule;

the at least one polynucleotide molecule comprising a secondary alcohol dehydrogenase gene operably linked to at least one promoter, wherein the co-cultured *Clostridium* and *B. subtilis* are capable of increased production of isopropanol compared to a co-culture with a non-transformed *B. subtilis* cell.

7. The method of claim 6, wherein the secondary alcohol dehydrogenase gene comprises a polynucleotide sequence having at least 80% sequence identity to the polynucleotide sequence set forth in SEQ ID NO: 1 and encoding the amino acid sequence set forth in SEQ ID NO: 10.

8. The method of claim 7, wherein the secondary alcohol dehydrogenase gene is a *Candida parapsilosis* secondary alcohol dehydrogenase (cpsadh) gene comprising the polynucleotide sequence set forth in SEQ ID NO: 1.

9. The method of claim 6, wherein the genetically engineered *B. subtilis* strain co-expresses a secondary alcohol dehydrogenase and a lipase.

10. The method of claim 6, wherein the *Clostridium* strain is *C. beijerinckii* G117 deposited according to ATCC Accession number PTA-121569.

11. The method of claim 6, wherein the medium is supplemented with glucose at a concentration of 60 g/L.

12. The method of claim 6, wherein the genetically engineered *B. subtilis* strain is cultured for a period of 24 hr before said co-culturing for a further period.

13. The method of claim 6, further comprising isolating said butanol and/or isopropanol.

* * * * *

SEQUENCE LISTING

<160> NUMBER OF SEQ ID NOS: 10

<210> SEQ ID NO 1
<211> LENGTH: 1011
<212> TYPE: DNA
<213> ORGANISM: Artificial Sequence
<220> FEATURE:
<223> OTHER INFORMATION: cpsadh

<400> SEQUENCE: 1
atgtcaatcc cgtcgtccca atacggcttt gtcttcaata aacagtctgg tctgaatctg 60
cgtaatgatc tgccggtcca taaaccgaaa gccggccagc tgctgctgaa agtcgatgca 120
gtgggtctgt gtcattctga cctgcacgtg atttatgaag gcctggattg cggtgacaac 180
tacgttatgg gccatgaaat tgcaggtacc gttgcagcag tcggtgatga cgtcatcaac 240
tataaagtgg gtgatcgtgt ggcgtgtgtt ggcccgaatg gttgcggcgg ttgtaaatac 300
tgccgcggcg ctatcgataa cgtgtgcaaa aatgcgtttg gtgattggtt cggcctgggt 360
tatgacggcg gttatcagca atacctgctg gttacccgtc cgcgcaacct gagccgtatt 420
ccggataatg tctctgctga cgtggcagct gcgagtaccg atgcggtcct gacgccgtat 480
cacgccatca aaatggcaca ggtttcaccg acctcgaaca ttctgctgat cggtgccggc 540
ggtctgggcg gtaatgcaat tcaagtggcc aaagcatttg gtgcgaaagt tacggtcctg 600
gataagaaaa aagaagcgcg tgatcaggcg aaaaaactgg gcgctgatgc ggtttatgaa 660
accctgccgg aaagcatttc tccgggtagt tttccgcct gttttgattt cgtgtcagtt 720
caggcaacgt tcgacgtttg ccaaaaatac gtcgaaccga aaggcgttat catgccggtc 780

-continued ggtctgggtg ctccgaacct gtcgtttaat ctgggtgatc tggcgctgcg tgaaattcgc 840
atcctgggca gcttctgggg taccacgaac gacctggatg acgtgctgaa actggtttcc 900
gaaggcaaag tgaaaccggt ggttcgttca gccaaactga aagaactgcc ggaatatatc 960
gaaaaactgc gtaacaatgc atacgaaggt cgcgtcgtct ttaacccgta a 1011

<210> SEQ ID NO 2
<211> LENGTH: 21
<212> TYPE: DNA
<213> ORGANISM: Artificial Sequence
<220> FEATURE:
<223> OTHER INFORMATION: Primer P01

<400> SEQUENCE: 2
gtcaatcccg tcgtcccaat a 21

<210> SEQ ID NO 3
<211> LENGTH: 21
<212> TYPE: DNA
<213> ORGANISM: Artificial Sequence
<220> FEATURE:
<223> OTHER INFORMATION: Primer P02

<400> SEQUENCE: 3
acgggttaaa gacgacgcga c 21

<210> SEQ ID NO 4
<211> LENGTH: 21
<212> TYPE: DNA
<213> ORGANISM: Artificial Sequence
<220> FEATURE:
<223> OTHER INFORMATION: Primer P03

<400> SEQUENCE: 4
tcccaattaa aggaggaagg a 21

<210> SEQ ID NO 5
<211> LENGTH: 16
<212> TYPE: DNA
<213> ORGANISM: Artificial Sequence
<220> FEATURE:
<223> OTHER INFORMATION: Primer P04

<400> SEQUENCE: 5
ctgccccggg gacgtc 16

<210> SEQ ID NO 6
<211> LENGTH: 27
<212> TYPE: DNA
<213> ORGANISM: Artificial Sequence
<220> FEATURE:
<223> OTHER INFORMATION: Barcode REC3-F

<400> SEQUENCE: 6
tcccaattaa aggaggaagg atccatg 27

<210> SEQ ID NO 7
<211> LENGTH: 28
<212> TYPE: DNA
<213> ORGANISM: Artificial Sequence
<220> FEATURE:
<223> OTHER INFORMATION: Barcode REC4-R

<400> SEQUENCE: 7

-continued

```
tgatctagag tcgacgtccc cggggcag                                         28


<210> SEQ ID NO 8
<211> LENGTH: 321
<212> TYPE: PRT
<213> ORGANISM: Artificial Sequence
<220> FEATURE:
<223> OTHER INFORMATION: Lipase B amino acid sequence
<220> FEATURE:
<221> NAME/KEY: misc_feature
<222> LOCATION: (313)..(313)
<223> OTHER INFORMATION: Xaa can be any naturally occurring amino acid

<400> SEQUENCE: 8

Met Ala Leu Pro Ser Gly Ser Asp Pro Ala Phe Ser Gln Pro Lys Ser
1               5                   10                  15

Val Leu Asp Ala Gly Leu Thr Cys Gln Gly Ala Ser Pro Ser Ser Val
            20                  25                  30

Ser Lys Pro Ile Leu Leu Val Pro Gly Thr Gly Thr Thr Gly Pro Gln
        35                  40                  45

Ser Phe Asp Ser Asn Trp Ile Pro Leu Ser Thr Gln Leu Gly Tyr Thr
    50                  55                  60

Pro Cys Trp Ile Ser Pro Pro Pro Phe Met Leu Asn Asp Thr Gln Val
65                  70                  75                  80

Asn Thr Glu Tyr Met Val Asn Ala Ile Thr Ala Leu Tyr Ala Gly Ser
                85                  90                  95

Gly Asn Asn Lys Leu Pro Val Leu Thr Trp Ser Gln Gly Gly Leu Val
            100                 105                 110

Ala Gln Trp Gly Leu Thr Phe Phe Pro Ser Ile Arg Ser Lys Val Asp
        115                 120                 125

Arg Leu Met Ala Phe Ala Pro Asp Tyr Lys Gly Thr Val Leu Ala Gly
    130                 135                 140

Pro Leu Asp Ala Leu Ala Val Ser Ala Pro Ser Val Trp Gln Gln Thr
145                 150                 155                 160

Thr Gly Ser Ala Leu Thr Thr Ala Leu Arg Asn Ala Gly Gly Leu Thr
                165                 170                 175

Gln Ile Val Pro Thr Thr Asn Leu Tyr Ser Ala Thr Asp Glu Ile Val
            180                 185                 190

Gln Pro Gln Val Ser Asn Ser Pro Leu Asp Ser Ser Tyr Leu Phe Asn
        195                 200                 205

Gly Lys Asn Val Gln Ala Gln Ala Val Cys Gly Pro Leu Phe Val Ile
    210                 215                 220

Asp His Ala Gly Ser Leu Thr Ser Gln Phe Ser Tyr Val Val Gly Arg
225                 230                 235                 240

Ser Ala Leu Arg Ser Thr Thr Gly Gln Ala Arg Ser Ala Asp Tyr Gly
                245                 250                 255

Ile Thr Asp Cys Asn Pro Leu Pro Ala Asn Asp Leu Thr Pro Glu Gln
            260                 265                 270

Lys Val Ala Ala Ala Ala Leu Leu Ala Pro Ala Ala Ala Ala Ile Val
        275                 280                 285

Ala Gly Pro Lys Gln Asn Cys Glu Pro Asp Leu Met Pro Tyr Ala Arg
    290                 295                 300

Pro Phe Ala Val Gly Lys Arg Thr Xaa Ser Gly Ile Val Thr Pro Ser
305                 310                 315                 320

Leu
```

<210> SEQ ID NO 9
<211> LENGTH: 963
<212> TYPE: DNA
<213> ORGANISM: Artificial Sequence
<220> FEATURE:
<223> OTHER INFORMATION: Lipase B DNA sequence
<220> FEATURE:
<221> NAME/KEY: misc_feature
<222> LOCATION: (937)..(937)
<223> OTHER INFORMATION: n is a, c, g, or t

<400> SEQUENCE: 9
atggcattgc cgtcaggttc tgacccggcc tttagccagc cgaagtctgt tctggatgct 60
ggcctgacat gtcagggtgc aagcccgtcg tccgtaagca aaccaattct gcttgtacca 120
ggcacgggca ctacgggccc gcagagcttt gattctaatt ggattcccct gtctacccag 180
cttgggtaca ccccttgttg gattagcccg cctcccttca tgctgaacga tacacaagtg 240
aatactgagt acatggtcaa cgcaattacc gccctttatg cgggaagtgg taacaataaa 300
cttcccgtgc tgacatggag tcagggggc ctggtggcac agtggggatt gacgtttttc 360
ccatcgatcc gctcgaaagt tgatcgtctg atggcatttg cgcctgatta taaaggcaca 420
gtgctcgcgg ggccattaga tgccctggct gtgtcagcac ctagtgtctg gcaacagacg 480
accggttccg cgctgacgac cgccctccgg aacgcaggtg gactgaccca aattgtgccg 540
acaaccaact tgtatagcgc caccgacgaa attgttcagc cgcaggtctc caattcgcct 600
ctcgattcaa gctatctgtt taacggcaaa aatgtacagg cacaggctgt ttgcgggcca 660
ttattcgtca tcgaccatgc cggtagctta acctcccagt tcagttacgt ggttggtcgc 720
tctgccctgc gtagtaccac gggccaagcg cgctcagcgg actacggtat cactgattgc 780
aatccgttac cggcgaatga cctgactccg gaacaaaagg tagcggctgc ggctttgtta 840
gcgccggccg ctgccgcgat tgtggcaggt cctaaacaaa actgtgaacc ggatctgatg 900
ccctatgccc gtccgtttgc ggtcggcaaa cgtactngct caggtatcgt tacgccaagc 960
tta 963

<210> SEQ ID NO 10
<211> LENGTH: 336
<212> TYPE: PRT
<213> ORGANISM: Artificial Sequence
<220> FEATURE:
<223> OTHER INFORMATION: cpsadh amino acid sequence

<400> SEQUENCE: 10

Met Ser Ile Pro Ser Ser Gln Tyr Gly Phe Val Phe Asn Lys Gln Ser
1 5 10 15

Gly Leu Asn Leu Arg Asn Asp Leu Pro Val His Lys Pro Lys Ala Gly
20 25 30

Gln Leu Leu Leu Lys Val Asp Ala Val Gly Leu Cys His Ser Asp Leu
35 40 45

His Val Ile Tyr Glu Gly Leu Asp Cys Gly Asp Asn Tyr Val Met Gly
50 55 60

His Glu Ile Ala Gly Thr Val Ala Ala Val Gly Asp Asp Val Ile Asn
65 70 75 80

Tyr Lys Val Gly Asp Arg Val Ala Cys Val Gly Pro Asn Gly Cys Gly
85 90 95

Gly Cys Lys Tyr Cys Arg Gly Ala Ile Asp Asn Val Cys Lys Asn Ala
100 105 110

Phe Gly Asp Trp Phe Gly Leu Gly Tyr Asp Gly Gly Tyr Gln Gln Tyr

-continued

```
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270

Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335
```